United States Patent
Linder et al.

(10) Patent No.: US 10,799,433 B2
(45) Date of Patent: Oct. 13, 2020

(54) FOAMING ANTIMICROBIAL COMPOSITIONS

(71) Applicant: S.C. Johnson & Son, Inc., Racine, WI (US)

(72) Inventors: Jessica Sue Haney Boester Linder, Belleville, IL (US); Althea Noel Johnson, Black Jack, MO (US); Nancy-Hope Elizabeth Kaiser, Collinsville, IL (US)

(73) Assignee: S. C. Johnson & Son, Inc., Racine, WI (US)

( * ) Notice: Subject to any disclaimer, the term of this patent is extended or adjusted under 35 U.S.C. 154(b) by 0 days.

(21) Appl. No.: 16/092,679

(22) PCT Filed: Apr. 18, 2017

(86) PCT No.: PCT/US2017/028154
§ 371 (c)(1),
(2) Date: Oct. 10, 2018

(87) PCT Pub. No.: WO2017/184614
PCT Pub. Date: Oct. 26, 2017

(65) Prior Publication Data
US 2019/0125634 A1 May 2, 2019

Related U.S. Application Data

(60) Provisional application No. 62/325,019, filed on Apr. 18, 2017, provisional application No. 62/412,521, filed on Oct. 25, 2016.

(51) Int. Cl.
| | |
|---|---|
| *A61K 8/04* | (2006.01) |
| *A61K 8/40* | (2006.01) |
| *A61K 8/41* | (2006.01) |
| *A61K 8/49* | (2006.01) |
| *A61K 8/55* | (2006.01) |
| *A61K 8/60* | (2006.01) |
| *A61K 8/86* | (2006.01) |
| *A61K 8/44* | (2006.01) |
| *A61K 8/893* | (2006.01) |
| *A61K 8/894* | (2006.01) |
| *A61K 8/34* | (2006.01) |
| *A61K 8/43* | (2006.01) |
| *A61K 8/73* | (2006.01) |
| *A61K 8/81* | (2006.01) |
| *A01N 25/30* | (2006.01) |
| *A01N 25/16* | (2006.01) |
| *A61Q 17/00* | (2006.01) |
| *A61Q 19/10* | (2006.01) |

(52) U.S. Cl.
CPC .............. *A61K 8/046* (2013.01); *A01N 25/16* (2013.01); *A01N 25/30* (2013.01); *A61K 8/345* (2013.01); *A61K 8/40* (2013.01); *A61K 8/41* (2013.01); *A61K 8/416* (2013.01); *A61K 8/43* (2013.01); *A61K 8/442* (2013.01); *A61K 8/4973* (2013.01); *A61K 8/55* (2013.01); *A61K 8/553* (2013.01); *A61K 8/602* (2013.01); *A61K 8/731* (2013.01); *A61K 8/8158* (2013.01); *A61K 8/86* (2013.01); *A61K 8/893* (2013.01); *A61K 8/894* (2013.01); *A61Q 17/005* (2013.01); *A61Q 19/10* (2013.01); *A61K 2800/596* (2013.01)

(58) Field of Classification Search
None
See application file for complete search history.

(56) References Cited

U.S. PATENT DOCUMENTS

| | | |
|---|---|---|
| 5,607,980 A | 3/1997 | McAtee et al. |
| 5,951,993 A | 9/1999 | Scholz et al. |
| 6,045,817 A | 4/2000 | Ananthapadmanabhan et al. |
| 6,083,517 A | 7/2000 | Ananthapadmanabhan et al. |
| 6,339,057 B1 | 1/2002 | Knox et al. |
| 6,352,701 B1 | 3/2002 | Scholz et al. |
| 6,423,239 B1 | 7/2002 | Cathey et al. |
| 6,562,360 B2 | 5/2003 | Scholz et al. |
| 6,583,103 B1 | 6/2003 | Klinkhammer |
| 6,610,315 B2 | 8/2003 | Scholz et al. |
| 6,616,922 B2 | 9/2003 | Taylor et al. |
| 6,723,689 B1 | 4/2004 | Hoang et al. |
| 6,881,757 B2 | 4/2005 | Moodycliffe et al. |
| 7,186,416 B2 | 3/2007 | Popp et al. |
| 7,268,165 B2 | 9/2007 | Greten et al. |
| 7,468,384 B2 | 12/2008 | Levy et al. |
| 7,521,404 B2 | 4/2009 | Luu et al. |
| 7,651,990 B2 | 1/2010 | Asmus |
| 7,670,615 B2 | 1/2010 | Veeger et al. |
| 7,683,018 B2 | 3/2010 | Koivisto et al. |
| 7,723,279 B2 | 5/2010 | Lestage et al. |
| 7,803,746 B2 | 9/2010 | Luu et al. |
| 7,842,725 B2 | 11/2010 | Wegner et al. |
| 7,985,773 B2 | 7/2011 | Greten et al. |

(Continued)

OTHER PUBLICATIONS

International Search Report and Written Opinion regarding Int'l. Appl. No. PCT/US2017/028154, dated Jul. 7, 2017, 11 pps.
Abstract of JP 2002-212051 (dated Jul. 31, 2002)—Pola Chem. Ind. Inc.

*Primary Examiner* — Sin J Lee

(57) ABSTRACT

A foaming antimicrobial composition, which includes a cationic antimicrobial, a combination of surfactants, skin conditioning agent(s), humectant(s), and water, is provided. The composition has excellent antimicrobial properties, while still maintaining skin hydration and mildness. Commonly, the foaming antimicrobial composition is triclosan-free.

7 Claims, 8 Drawing Sheets

(56) References Cited

U.S. PATENT DOCUMENTS

| | | |
|---|---|---|
| 8,053,399 B2 | 11/2011 | Seidling et al. |
| 8,124,115 B2 | 2/2012 | Veeger et al. |
| 8,193,136 B2 | 6/2012 | Taylor et al. |
| 8,263,098 B2 | 9/2012 | Fernandez de Castro et al. |
| 8,388,991 B2 | 3/2013 | Sondgeroth et al. |
| 8,795,697 B2 * | 8/2014 | Brown ............... A61K 8/0204 424/401 |
| 9,090,855 B2 | 7/2015 | Polzin et al. |
| 9,095,134 B2 | 8/2015 | Eder et al. |
| 9,276,714 B2 | 2/2016 | Hardy et al. |
| 9,956,153 B2 | 5/2018 | Emiru et al. |
| 2003/0022941 A1 | 1/2003 | Taylor et al. |
| 2003/0069317 A1 | 4/2003 | Seitz, Jr. et al. |
| 2006/0039942 A1 | 2/2006 | Greten et al. |
| 2006/0275218 A1 | 12/2006 | Tamarkin et al. |
| 2007/0179207 A1 | 3/2007 | Fernandez de Castro |
| 2009/0018213 A1 | 1/2009 | Snyder et al. |
| 2009/0098067 A1 | 4/2009 | Seidling et al. |
| 2009/0226498 A1 | 9/2009 | Flugge-Berendes et al. |
| 2009/0326076 A1 | 12/2009 | Asmus |
| 2010/0183519 A1 | 7/2010 | Katz et al. |
| 2010/0216889 A1 | 8/2010 | Modak et al. |
| 2010/0234775 A1 | 9/2010 | Yasuhara et al. |
| 2011/0152150 A1 * | 6/2011 | Bernard ............... A61K 8/046 510/136 |
| 2011/0206630 A1 | 8/2011 | Rude |
| 2011/0305739 A1 * | 12/2011 | Royce ............... A61K 8/0295 424/401 |
| 2012/0021025 A1 | 1/2012 | Bendejacq et al. |
| 2013/0210923 A1 | 8/2013 | Zhu |
| 2014/0100288 A1 | 4/2014 | Deszalay |
| 2014/0171513 A1 | 6/2014 | Seidling et al. |
| 2014/0378550 A1 | 12/2014 | Grundhofer |
| 2015/0073051 A1 | 3/2015 | Cohen et al. |
| 2015/0148425 A1 | 5/2015 | Fuls et al. |
| 2015/0320041 A1 | 11/2015 | Heisig et al. |
| 2016/0030315 A1 | 2/2016 | Emiru et al. |

\* cited by examiner

FOAMING ANTIMICROBIAL COMPOSITIONS

CROSS-REFERENCE TO RELATED APPLICATIONS

This application is a U.S. national stage of international application PCT/US2017/028154, filed on Apr. 18, 2017, which claims priority to U.S. Provisional Patent Application Ser. No. 62/325,019, filed on Apr. 20, 2016, and Ser. No. 62/412,521, filed on Oct. 25, 2016, the entire contents of which are herein incorporated by reference.

BACKGROUND

A large number of antimicrobial handwashing compositions are known in the art. Anti-microbial handwashing compositions are available as consumer grade, personal care products and professional grade for use in a large number of industries including, but not limited to, the food and beverage manufacturing, pharmaceutical manufacturing, healthcare and medical services and manufacturing, and biological and chemical warfare decontamination industries, where control and/or elimination of microbes, particularly on the skin, is critical.

In many industries, antimicrobial control and/or elimination, particularly on body skin surfaces, is performed routinely by personnel in the course of performing their jobs. Frequent handwashing is commonplace and required, and there is an increasing need for antimicrobial compositions that cover a broad spectrum of microbes while still protecting and maintaining the integrity of the skin.

Many classes of antimicrobial agents are known in the art. "Active" antimicrobials include without limitation: alcohols, particularly the lower alcohols, iodine, peroxides, phenolic compounds, carbanalide compounds, surface active agents, halogens, carboxylic acids and esters, quaternary ammonium compounds, biguanides, acetophenones, and the like. Particularly popular antimicrobials include: triclosan, chlorhexidine gluconate and other salts, povidone-iodine, benzethonium chloride, benzalkonium chloride and ethanol. While effective, many of these active agents are themselves irritating to the skin or are combined with components that are skin irritants. They may also be incompatible with certain components, leading to a loss of efficacy of the antimicrobial active. In addition, while triclosan has been a dominant antimicrobial active ingredient in the skin cleanser market, there has been increasing scrutiny with respect to triclosan use due to environmental, health and safety concerns based on formation of intermediate byproducts not viewed as "friendly" to the environment.

A continuing need exists for antimicrobial compositions that are highly effective, but free of health, safety and environmental concerns. Such compositions may desirably be effective as cleansing (washing) compositions and impart moisturizing and aesthetic effects, such as mildness and skin feel, to the skin, without loss of antimicrobial activity.

SUMMARY

The present disclosure relates generally to foaming antimicrobial compositions comprising an antibacterial agent, skin conditioning agent(s), and typically a blend of surfactants, which may be present at relatively low concentrations in comparison to traditional antimicrobial products. Commonly, the compositions are efficacious against a variety of microbes including those often encountered in a hospital or other healthcare environment, while still retaining mildness and other aesthetic properties compared to other known antimicrobial compositions. Many of the prior and existing known antimicrobial compositions sacrifice mildness for efficacy and vice versa. In addition, while many achieve antimicrobial effects, they lack aesthetic skin feel effects resulting in a "tacky" after-use feel. The present compositions are desirably highly efficacious with superior mildness as compared to other known antimicrobial handwashing compositions, even in view of the relatively low surfactant levels utilized. Preferably, the compositions are essentially free or free of triclosan. In some embodiments, the composition may be free of high levels of lower molecular weight alcohol, such as ethanol, that can dry or irritate the skin. That is, the compositions may include small amounts of lower molecular weight alcohol such as ethanol.

In one aspect the present technology provides foaming antimicrobial compositions for use as alternatives to existing triclosan containing products, which may be used as a handwashing composition. The present foaming antimicrobial compositions are preferably effective against a broad spectrum of microbes, while remaining mild to the skin.

Typically, the present compositions meet both the 1 and 10 log reduction criteria for the FDA Healthcare Personnel Handwash from the Jun. 17, 1994 Tentative Final Monograph ("TFM") for Healthcare Antiseptic Drug Products, 21 C.F.R. Parts 333 and 369, as well as additional log reduction criteria from the May 1, 2015 amendment to the TFM. Preferably, the compositions are statistically significantly milder than market-leading parachlorometaxylenol (PCMX) and benzalkonium chloride products. In some embodiments, the compositions are triclosan-free.

The present compositions utilize a cationic antimicrobial component. For example, the composition may include benzalkonium chloride as the "active" antimicrobial. Surprisingly, benzalkonium chloride is capable of achieving required antimicrobial efficacy for healthcare, while remaining mild to the skin. As such, benzalkonium chloride is highly desired not only for antimicrobial effects, but also its desired aesthetic effects. In some embodiments, the composition may include certain adjuvant components that may have some antimicrobial activity alone or provide a synergistic effect in combination with benzalkonium chloride. Other antimicrobial components may be utilized but are not required to achieve FDA criteria.

Additional components of the compositions commonly include a combination of amine oxide and other surfactants that are compatible with cationic components of the composition, humectants, emollients, skin conditioning agents, and water. Low levels of solvents other than water may also be used. The pH of the compositions is typically about 6 to 7 and, often, about 6.5.

In some embodiments, the present compositions achieve excellent foaming action and foam stability. A unique combination of amine-oxide surfactants, coupled with skin moisturizing and skin feel agents, may desirably provide a highly efficacious composition that produces a dense creamy foam and achieves superior mildness over known compositions.

In some embodiments, the present technology provides a foaming antimicrobial composition having excellent cleansing, antimicrobial and skin moisturizing properties over presently available compositions. In some embodiments, the composition may be a handwashing composition. Desirably, the antimicrobial composition meets or exceeds FDA criteria for healthcare personnel antiseptic handwashes. Preferably, the present compositions provide an alternative to existing commercial triclosan-based compositions, particularly in view of current environmental and health and safety concerns associated with triclosan use.

In one embodiment, the composition is a foaming antimicrobial composition comprising:
  i) a quaternary ammonium compound, such as benzalkonium chloride;
  i) a mixture of surfactants that include amine oxides;
  iii) humectants;
  iv) skin conditioning agents comprising cationic and/or nonionic polymers;
  v) buffers; and
  vi) water.
  i) a quaternary ammonium compound, such as benzalkonium chloride;
  i) a mixture of surfactants that include amine oxides and zwitterionic surfactant(s);
  iii) humectants;
  iv) skin conditioning agents comprising cationic and/or nonionic polymers;
  v) buffers; and
  vi) water.

In another aspect, the present technology provides a foaming, antimicrobial composition, comprising:
  a. a cationic antimicrobial component;
  b. a surfactant combination comprising two or more tertiary amine oxide surfactants, an alkyl glycoside and/or PEG-based nonionic surfactant, and zwitterionic surfactant;
  c. skin conditioning agent;
  d. foam stabilizer; and
  e. water.

In another embodiment is provided an antimicrobial composition, comprising:
  a. a cationic antimicrobial component;
  b. tertiary amine oxide surfactant comprising a tertiary fatty amine oxide and a fatty acid amidoalkyl tertiary amine oxide;
  c. alkyl glycoside and/or PEG-based nonionic surfactant;
  d. $C_{10}$-$C_{16}$ fatty acid isopropanolamide;
  e. water-soluble silicone polymer;
  f. humectant; and
  g. at least about 75 wt % water.

In one aspect, the foaming, antimicrobial composition may include antimicrobial benzyl quaternary ammonium salt; tertiary amine oxide surfactant, which includes tertiary fatty amine oxide and fatty acid amidoalkyl tertiary amine oxide; alkyl glycoside; $C_{10}$-$C_{16}$ fatty acid isopropanolamide; quaternary ammonium phospholipid zwitterionic surfactant; water-soluble polyethyleneglycol polysiloxane; PEG-based nonionic polymer; humectant; and at least about 80 wt % water. In such compositions, the combined amount of the tertiary amine oxide surfactants, the isopropanolamide, the zwitterionic surfactant and the alkyl glycoside may desirably constitute no more than about 2.5 wt. %, no more than about 2.0 wt. % and, often, no more than about 1.7 wt. % of the composition.

In another aspect, the foaming, antimicrobial composition may include a cationic antimicrobial component; tertiary amine oxide surfactant, which includes a tertiary fatty amine oxide and a fatty acid amidoalkyl tertiary amine oxide; alkyl glycoside and/or PEG-based nonionic surfactant; zwitterionic surfactant; $C_{10}$-$C_{16}$ fatty acid isopropanolamide; water-soluble silicone polymer; humectant; and at least about 75 wt % water. The composition may also include a PEG-based nonionic polymer, such as an PEG-150 fatty acid diester. For example, such an antimicrobial composition may include about 0.3 to 1.0 wt. % of the cationic antimicrobial component; about 0.5 to 2 wt. % of the tertiary amine oxide surfactant; about 0.2 to 1 wt. % of the alkyl glycoside; about 0.05 to 0.3 wt. % zwitterionic surfactant; about 0.05 to about 0.5 wt. % of the $C_{10}$-$C_{16}$ fatty acid isopropanolamide; about 0.5 to 2 wt. % of the water-soluble silicone polymer; about 1 to 5 wt. % humectant; and about 0.5 to 2 wt. % of a PEG-based nonionic polymer.

Commonly, the compositions may be pumped or otherwise mechanically dispensed. Optionally, polymeric thickeners may be utilized in the compositions. Thickeners increase viscosity and allow the composition to be dispensed as a thick liquid that stays on the hands.

In another embodiment, the present technology provides a method of providing effective antimicrobial action on the skin, while desirably maintaining mildness, moisturization and/or aesthetic skin feel properties, through use of the above composition.

The composition may be air foamed, i.e., pumped mechanically, to produce a foaming handwashing composition, or provided as a liquid or gel.

Figure 1:
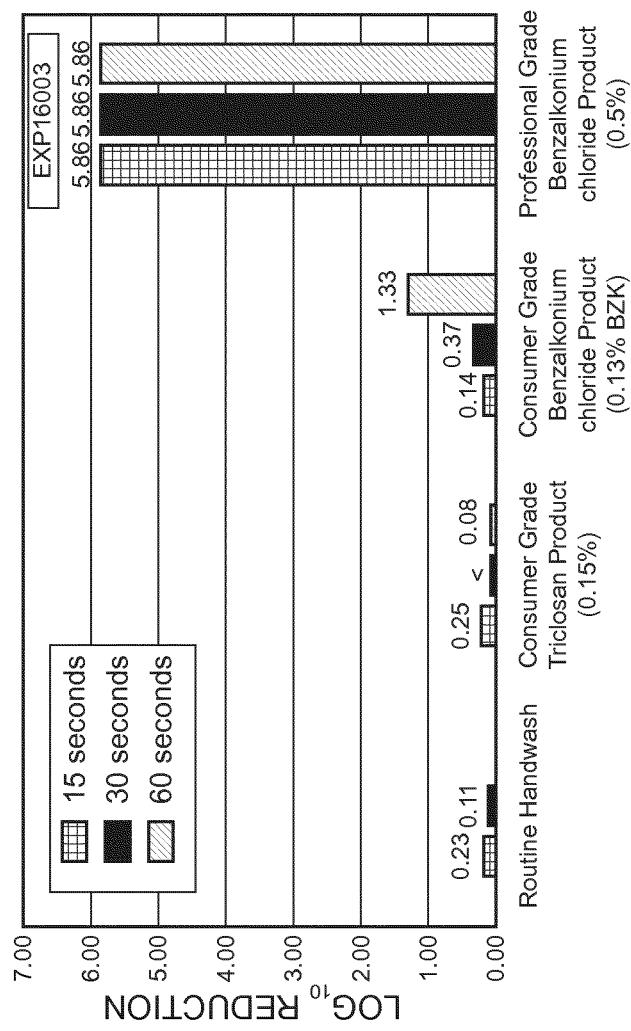
FIG. 1 is a bar graph showing the log reduction of *Klebsiella pneumoniae* BAA-1705 strain in an in vitro time kill test using Composition A ("EXP16003") in comparison to two consumer grade handwashing soaps—a triclosan-based (0.15%) soap and a consumer grade soap containing 0.13% benzalkonium chloride.

(ATCC No. 14756) (log CFU recovery) of a comparison between Composition B and Hibiclens® liquid antimicrobial skin soap.

DETAILED DESCRIPTION

The present technology provides antimicrobial compositions that can be highly effective in antimicrobial elimination or reduction while remaining non-irritating to the skin. In some embodiments, the compositions may be effectively used handwashing compositions. Preferably, the compositions are efficient cleansing compositions producing large volumes of dense, creamy foam that has a lubricious substantive feel during washing, even at relatively low levels of active surfactant. The compositions can often moisturize the skin by providing hydration and softness and have a positive impact on the after feel.

The compositions are an alternative to triclosan-containing compositions, which are under increasing scrutiny due to environmental, health and safety concerns. In some embodiments, the compositions are also essentially free of lower molecular weight alcohol (e.g., ethanol) and other components that can dry or irritate the skin.

An embodiment of the composition comprises: a triclosan-free antimicrobial component, surfactants that are compatible with cationic components, skin conditioning agents, humectants, emollients, buffers and water. Low levels of solvents may also be utilized to improve solvency of certain components. In another embodiment, thickeners may also be included.

Antimicrobials useful in the present compositions include, without limitation, cationic antimicrobial components such as quaternary ammonium compounds and salts thereof, biguanides, substituted biguanides, povidone iodine, and peroxide compounds. Especially preferred are quaternary ammonium compounds having the general structural formula

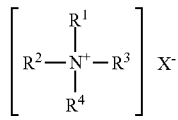

wherein at least one of $R^1$, $R^2$, $R^3$ and $R^4$ is an alkyl, aryl or an alkylaryl substituent having from 6-26 carbon atoms. Benzalkonium chloride is an especially preferred quaternary ammonium compound for use in the compositions.

The antimicrobial compound may be present up to 5 wt. %, based on the total wt. % of all components in the antimicrobial composition. In some embodiments, the antimicrobial compound is present in amounts ranging from about 0.1 to 3.0 wt. %. In some embodiments, the antimicrobial compound may be present in amounts ranging from about 0.3 to 1.0 wt. %. As used herein unless otherwise specified, the term "wt. %" refers to the amount of actual specified component and not to the wt. % of the commercial version as sold (e.g., where the commercial product is a 50% aqueous solution, the wt. % of the specific component would be half the amount of the commercial product included in the foaming antimicrobial composition).

The primary surfactants used in the compositions typically include nonionic surfactants. Non-limiting examples of nonionic surfactants include amine oxides, fatty acid amides, fatty alcohols, ethoxylated fatty alcohols, block copolymers of polyethylene glycol and polypropylene glycol, glycerol alkyl esters, alkyl polyglucosides, quaternized alkyl polyglucosides, polyoxyethylene and polyoxypropylene glycol alkyl ethers, polyoxyethylene glycol octylphenol ethers, polyoxyethylene glycol alkylphenol ethers, sorbitan alkyl esters, polyoxyethylene glycol sorbitan alkyl esters, and mixtures thereof. It is expected that a wide variety of surfactants may be useful, provided that they do not interfere with the efficacy of cationic components. One skilled in the art would know of additional useful surfactants based upon the disclosure herein.

Particularly useful surfactants for the compositions include without limitation amine oxides, isopropanolamides, alkyl polyglucosides, EO/PO block copolymers, poloxamers, and the like.

In some embodiments the amine oxides may be present in amounts ranging from about 0.2 to 3.0 wt. % and often, about 0.5 to 2.0 wt. %. In some embodiments, the compositions may include a tertiary amine oxide surfactant such as a tertiary fatty amine oxide and/or a fatty acid amidoalkyl tertiary amine oxide. Preferred amine oxides include, but are not limited to, laurylamidopropyl dimethylamine oxide, myristylamidopropyl dimethylamine oxide, lauramine oxide, soyamidopropyl amine oxide, cocamidopropyl amine oxide, and mixtures thereof. Other useful amine oxides are known to one skilled in the art.

In some embodiments, the isopropanolamide may be present in amounts ranging from about 0.05 to 1 wt. % and often, about 0.1 to 0.5 wt. %. Preferred isopropanolamides include $C_{10}$-$C_{16}$ fatty acid isopropanolamides. A suitable isopropanolamide includes, but is not limited to, cocamide monoisopropanolamide (cocamide MIPA).

In some embodiments, the compositions may include alkyl glycoside. At times, the alkyl glycoside may be present in amounts ranging from about 0.1 to 2 wt. % and often, about 0.25 to 1 wt. %. Suitable alkyl glycosides include alkyl glucosides, such as decyl glucoside, sodium lauryl glucose carboxylate, lauryl glucoside and capryl glucoside.

In some embodiments, the compositions may include a PEG-based nonionic surfactant such as polyoxyethylene and polyoxypropylene glycol alkyl ethers, polyoxyethylene glycol octylphenol ethers, polyoxyethylene glycol alkylphenol ethers, sorbitan alkyl esters, polyoxyethylene glycol sorbitan alkyl esters, and mixtures thereof. In some embodiments, the PEG-based nonionic surfactant may be present in amounts ranging from about 0.5 to 2.5 wt. %. Suitable PEG-based nonionic surfactants include polyethyleneglycol sorbitan fatty acid ester (e.g., PEG-80 sorbitan) and polyethyleneglycol fatty acid diester (e.g., PEG distearate).

A wide variety of suitable EO/PO block copolymers and polyethyleneglycol-based ("PEG-based") polymers are known in the art, including, but not limited to, poloxamers. In some embodiments, the antimicrobial compositions may include a PEG-based nonionic polymer, e.g., an PEG fatty acid diester having an average of about 100 to 200 ethylene glycol subunits, such as PEG-150 distearate.

Suitable cationic surfactants include, but are not limited to, polyquaternium compounds and salts thereof and monoalkyl amine and dialkyl amine derivatives of quaternary ammonium compounds. These surfactants may also function as skin conditioner components. Particularly useful cationic surfactants include without limitation polyquaterary ammonium polymers, e.g., cationic acrylamide-based polymer such as polyquaternium-7.

Amphoteric and zwitterionic surfactants that do not interfere with the cationic antimicrobial components may be used in the compositions and include without limitation: betaines, glycinates, imidazolines, imidazoline derivatives, hydroxysultaines and combinations thereof. Some zwitterionic surfactants, such as quaternary ammonium phospholipids (e.g., cocamidopropyl dimonium chloride phosphate), may also function as a skin conditioning agent. In some embodiments, the composition may include about 0.05 to 0.3 wt. % of the quaternary ammonium phospholipid.

Similarly, anionic surfactants that do not interfere with the cationic components are also useful. Suitable anionic surfactants include, but are not limited to, alcohol phosphates and phosphonates, octoxynol phosphates, non-oxynol phosphates, sulfates, sulfonates, alkyl carboxylates, alkyl ether carboxylates, alkyl alkoxy carboxylates, ethoxy carboxylates, taurates, fatty taurides, succinamates, lactylates and sarcosinates.

Surprisingly, it has been found that very low levels of active surfactant may be utilized in the present composition without sacrificing cleansing, foaming ability, foam density, foam stability, skin feel while washing and after feel, and the like. In some embodiments, the compositions may comprise active surfactant levels of about 3 wt. % or less, about 2 wt. % or less or in some instances no more than about 1.7 wt. % active surfactant.

A particularly preferred active surfactant system includes lauramine oxide, soyamidopropyl amine oxide, cocamidopropyl amine oxide, decyl glucoside, cocamidopropyl PG-dimonium chloride, and Cocamide MIPA. Cocamide MIPA, while typically used as a surfactant, may also function as a foam booster in the present compositions. For higher viscosity (thickened) compositions, PEG-80 sorbitan laurate was found to be one of the few surfactants that foamed in the presence of a thickener, while maintaining antimicrobial efficacy. In some embodiments, PEG-80 sorbitan laurate may be substituted for decyl glucoside in a thicker composition.

Typical, but non-limiting, surfactant compositions useful in the compositions are set forth below:

| Surfactant System Concentrations | |
|---|---|
| Wt % Surfactant of Composition with Cocamide MIPA | Wt % Surfactant of Composition without Cocamide MIPA |
| 1.53% | 1.33% |

Even with the low weight percent surfactant, the compositions typically have a desirable foam profile both as dispensed and during washing. This was achieved by blending surfactants, foam boosters, and foam stabilizers. The lauramine oxide may provide flash foam and foam build. However, this material is often purposefully kept at low active concentrations as it can cause drying through stripping of lipids at higher concentrations. The cocamidopropyl amine oxide may be selected because it may help to boost the flash foam and add to foam build while providing some skin conditioning. The soyamidopropyl amine oxide, unlike other soy based materials, may actually contribute to foam build instead of hindering it. The soyamidopropyl amine oxide may also add a more luxurious feel to the foam that is produced and provide skin conditioning benefits that help to mitigate the stripping of lipids that can occur through normal handwashing. The decyl glucoside may act as a mild cleanser and aid in foam build during washing. The cocamidopropyl PG-dimonium chloride phosphate can add somewhat to foam build and impart a soft silky after feel. The Cocamide MIPA may help to boost and stabilize the foam. Both PEG-150 distearate and cetyl hydroxyethyl cellulose may work to stabilize the foam during washing, as well as adding to the mildness of the system.

Humectants and emollients are useful skin conditioning agents that moisturize and protect the skin and provide a lasting, soft conditioned after feel. The present composition may include one or more such components. Commonly, humectants include, but are not limited to, aliphatic alcohols, polyhydroxy alcohols, glycols, polyols, sorbitol, and ureas. Useful emollients include, but are not limited to, silicone polymers, phospholipid complexes, esters, fatty acids, alcohols, glycols, and polyols. Other humectants and emollients useful in the compositions are known in the art. In some embodiments, the compositions may include about 1 to 15 wt. % humectant(s). Preferably, the compositions may include hexylene glycol, glycerin, and/or sorbitol.

Other useful skin feel components and conditioners include, but are not limited to, water soluble silicone polymers, such as dimethicones, cationic polymers, and nonionic polymers, such as certain cellulosic materials. Particularly useful components include polyquaternium-7, cetyl hydroxyethylcellulose, PEG-8 dimethicone. In some embodiments, the compositions may include a water soluble silicone polymer such as PEG-8 dimethicone. Preferably, the composition includes about 0.5 to 2 wt. % of a water soluble silicone polymer. In some embodiments, the compositions may include a cationic acrylamide based polymer. Preferably the cationic acrylamide based polymer is an acrylamide/diallyldimethylammonium chloride copolymer, such as polyquaternium-7. In some embodiments, the composition may include about 0.05 to 0.3 wt. % of a cationic acrylamide based polymer. In some embodiments, the compositions may include about 0.1 to 2 wt. % of a cellulosic material (i.e., cellulose derivative). Preferably, the cellulosic material may be cetyl hydroxyethylcellulose or hydroxypropyl methylcellulose.

Other adjuvants may be used in the compositions, provided that they do not negatively affect the antimicrobial or skin aesthetic properties of the composition. Adjuvants include solvents, buffers, chelating agents, preservatives, thickeners, viscosity modifiers, such as certain cellulosic compounds, particulate fillers, dyes, pigments, fragrances, and additional antimicrobial agents, not including triclosan. In some embodiments, a preservative may be present in a range from about 0.05 to 1 wt. %. In some embodiments, a buffer may be present in a range from about 0.01 to 0.1 wt. %. A non-limiting buffer includes citric acid or a salt thereof.

The compositions typically include at least about 75 wt. % water. In some embodiments, the compositions include at least about 80 wt. % water or often at least about 85 wt. % water.

An illustrative embodiment of the composition is set forth below in Table IA.

TABLE IA

Formulation of Composition A

| Component | Formula (Wt. %) | Wt. % as Active |
|---|---|---|
| Soft water | 82.735 | 86.73 |
| Hexylene Glycol | 6.000 | 6.00 |
| Glycerin (96% active) | 2.000 | 1.92 |
| PEG-8 Dimethicone | 1.000 | 1.00 |
| PEG-150 Distearate | 0.950 | 0.95 |
| Sorbitol (70% active) | 0.750 | 0.525 |
| Decyl Glucoside (50% active) | 1.000 | 0.500 |
| Benzalkonium Chloride (50% active) | 1.000 | 0.500 |
| Soyamidopropyl amine oxide (30% active) | 1.000 | 0.300 |

TABLE IA-continued

Formulation of Composition A

| Component | Formula (Wt. %) | Wt. % as Active |
|---|---|---|
| Cocamide MIPA | 0.200 | 0.200 |
| Cetyl hydroxyethylcellulose | 0.200 | 0.200 |
| Polyquaternium 7 (10%) | 1.000 | 0.100 |
| Lauramine oxide (30% active) | 0.600 | 0.180 |
| Cocamidopropyl amine oxide (30% active) | 0.750 | 0.225 |
| Cocamidopropyl PG-Dimonium Chloride phosphate (50% active) | 0.250 | 0.125 |
| Citric Acid | 0.030 | 0.030 |
| Potassium Hydroxide (45% active) | 0.035 | 0.016 |
| Phenoxyethanol | 0.500 | 0.500 |

Another illustrative embodiment is set forth below in Table 1B.

TABLE IB

Formulation of Composition B

| Component | Formula (Wt. %) | Wt. % as Active |
|---|---|---|
| Soft water | 85.8300 | 90.0360 |
| Hexylene Glycol | 2.0000 | 2.0000 |
| Cocamidopropyl amine oxide (30% active) | 3.0000 | 0.9000 |
| PEG-80 Sorbitan Laurate | 1.5000 | 1.5000 |
| Hydroxypropyl Methylcellulose | 1.0000 | 1.0000 |
| PEG-150 Distearate | 1.0000 | 1.0000 |
| PEG-8 Dimethicone | 1.0000 | 1.0000 |
| Benzalkonium Chloride (50% active) | 1.4000 | 0.7000 |
| Sorbitol (70% active) | 0.5000 | 0.3500 |
| Glycerin (96% active) | 0.2500 | 0.2400 |
| Cocamidopropyl PG-Dimonium Chloride Phosphate (50% active) | 0.3000 | 0.1500 |
| Soyamidopropyl Amine Oxide (30% active) | 0.7500 | 0.2250 |
| Lauramine Oxide (30% active) | 0.8000 | 0.2400 |
| Phenoxyethanol | 0.5000 | 0.5000 |
| Cocamide MIPA | 0.1500 | 0.1500 |
| Potassium Hydroxide (45% active) | 0.0200 | 0.0090 |
| Citric Acid (pH adjustment only) | 0.0000 | 0.0000 |

The primary differences between Table 1A's formulation and Table 1B's formulation is the existence of a cellulosic thickener in the 1B formulation and the addition of a surfactant that foamed in the presence of the thickener without lowering antimicrobial activity substantially.

The components set forth in Tables 1A and 1B and their general contributions are hereinafter described.

Benzalkonium Chloride is a quaternary ammonium-based ingredient that is available commercially from Lonza as Lonzagard BKC cGMP as 50 wt % solution in 5% aqueous ethanol. Desirably, it provides a majority of the microbial efficacy for the compositions and improves the overall solubility profile of the composition. It also may enhance the feel while washing.

Phenoxyethanol is a glycol ether that commonly serves as a preservative in many compositions and may improve microbial activity against *S. marcescens* and *C. albicans*. It also gives the product a rose note smell. It is available from BASF as Bronidox 1160 and Dow as Dowanol EPH. Phenoxyethanol is also known to have synergistic antimicrobial effects with a variety of traditional antimicrobials, including benzalkonium chloride, even at very low levels. In some embodiments, phenoxyethanol may be present in a range from about 0.05 to 1 wt. %.

PEG-150 Distearate is a polymeric polyethylene glycol diester of stearic acid. Preferably, it provides foam stability, substantial feel while washing, and/or some emolliency. It may also help to pull less soluble materials into solution. It is available from Vantage as Lipopeg 6000-DS.

Cocamide MIPA is a nonionic surfactant that is a mixture of isopropanolamides of coconut acid. It may boost and stabilize the foam as well as add to the substantivity of the product during washing. It is available from Solvay as Mackamide CPA and Stepan as Ninol M10.

Lauramine oxide (dodecyldimethylamine oxide) is a 30 wt % solution of straight chain $C_{12}$ tertiary amine oxide available from Solvay as Mackamine LO and BASF as Mazox LDA. Desirably, it provides lipid cleansing, flash foam, and/or a dense foam build.

Soyamidopropyl amine oxide is a $C_{16}$-$C_{18}$-alkyl amidopropyl tertiary amine oxide. It can provide flash foam, a creamy feel while washing, and/or contribute to soft after feel. It is available from Lubrizol as Chemoxide SO as 30 wt % solution.

Cocamidopropyl amine oxide is a $C_8$-$C_{18}$-alkyl amidopropyl tertiary amine oxide. It can provide cleaning, flash foam, and/or contribute to the substantial feel while washing. It is available from Southern Chemical and Textile as Techmine 350 as 30 wt % solution.

PEG-80 Sorbitan laurate is an ethoxylated sorbitan monoester of lauric acid with an average of 80 moles of ethylene oxide. Preferably it improves the foam profile of the compositions and/or enhances the substantial feel while washing. It is available from Solvay as Alkamuls PSML-80/72 LD.

Decyl glucoside is a $C_8$-$C_{16}$ alkyl polyglucoside. This nonionic surfactant desirably provides mild cleaning and/or flash/sustained foam. It is available from Dow as a 50 wt % solution (EcoSense 3000).

Cocamidopropyl dimonium chloride phosphate is a zwitterionic surfactant that is quaternary ammonium-based phospholipid. It may contribute to the foam while washing and/or provide a lasting soft, conditioned after feel. It is available as a 50 wt. % aqueous solution from Croda as Arlasilk PTC-LQ-(AP) and Colonial as Cola Lipid C.

Cetyl hydroxethylcellulose is a water soluble polymer of the ether of cetyl alcohol and hydroxyethylcellulose. Commonly, this material acts as an emollient that improves the after feel and/or improves the substantivity and slip during washing. It is available from Ashland as Natrosol Plus 330 CS.

Hydroxypropyl methylcellulose is a water soluble polymer of the propylene glycol ether of methyl cellulose. It acts as a thickener that typically improves the substantivity and slip during washing. It is available from Dow as Methocel K15M Premium.

Citric acid is a polyprotic acid that acts as a pH adjuster to help disperse cellulose derivates such as cetyl hydroxethylcellulose. It may also serve as a buffer to maintain the final product pH. It is available from multiple suppliers.

Potassium hydroxide is commonly available as a 50 wt. % aqueous solution and is an inorganic base that can serve as a pH adjuster/buffer. The material may also aid in the hydration of cetyl hydroxyethylcellulose. It is available from multiple suppliers.

Glycerin is an alcohol sugar that acts as a humectant. Typically, it moisturizes by bringing water to the skin, providing hydration and softness. It is available from multiple suppliers.

Sorbitol is a hexahydric sugar alcohol that acts as a humectant. Typically, it moisturizes by bringing water to the skin, providing hydration and softness. It is a colorless liquid that is available commercially from Roquette and the Archer Daniels Midland Co., among other suppliers, as a 70 wt % solution.

Hexylene glycol is an aliphatic alcohol that acts as a humectant and co-solvent. Typically, it moisturizes by bringing water to skin; positively impacting the after feel. It also may provide solvency to the system and/or help to ensure the BZK active is not tied up by the surfactants. It is a colorless, viscous liquid. It is commercially available in pure form from Penta Manufacturing, Solvay and Haltermann, among other suppliers.

Polyquaternium 7 is a cationic copolymer of acrylamide and diallyldimethyl-ammonium chloride. It may act as a film former skin conditioner and/or improve the lubricious feel of the product, specifically on the back of hands and over fingernails. It is available from Lubrizol as Merquat 550 and by Solvay as Mackernium 0075.

PEG-8 Dimethicone is a polyethylene glycol of dimethicone containing an average of 8 moles of ethylene oxide. This water soluble silicone polymer may serve as a skin conditioner that improves the lubricity during washing, lessens tack on wet to dry transition, and/or improve long term after feel of product. It is a available from Biosil Technologies as Biowax 754.

General non-limiting ranges for product specifications of the compositions are set forth below:

Composition A

| Specification | Target Range | Test Method |
|---|---|---|
| Color | Colorless to Straw | QC-110 |
| Clarity (@ 25 C.) | Clear to slightly hazy | QC-107 |
| pH | 6.3-6.7 | QC-106/AN076 |
| Specific Gravity | Record (1.011 Typical) | QC-114 SOPIC484 |
| Viscosity (@ 25 ± 0.1° C., small same adapter, spindle S18, @ 60 rpm) | Record (11-19 cps typical) (Alert Limit <5 cps or >20 cps) (Action Limit ≥21 cps) | QC-105/AN066 |
| BZK Assay | 0.490-0.510% | TBD/AN253 |

Composition B

| Specification | Target Range | Test Method |
|---|---|---|
| Color | Colorless to Straw | QC-110 |
| Clarity (@ 25 C.) | Clear to slightly hazy | QC-107 |
| pH | 6.3-6.8 * | QC-106/AN076 |
| Specific Gravity | Record (1.0098 Typical) * | QC-114 SOPIC484 |
| Viscosity (@ 25 ± 0.1° C., small same adapter, spindle S31, @ 12 rpm) | Record (1000-1500 cps typical) (Alert Limit <1000 cps or >2000 cps) (Action Limit ≥700 cps or ≥3000) | QC-105/AN066 |
| BZK Assay | 0.679-0.735% | AN255 |

Generally, no specific manufacturing guidelines or techniques are needed to prepare the compositions. Suitable manufacturing techniques to produce the compositions are known. Notwithstanding preparation of the compositions is not a matter of simple mixing or routine experimentation.

Cocamide MIPA commonly exhibits the best dissolution at temperatures above about 122° F. (range 125°-140° F.) and will readily incorporate with some mixing. If added at lower temperatures (minimum of 113° F.), longer mix times may be required. If the temperature of addition is too high, the material may degrade, negatively impacting the foam profile of the product.

Cetyl hydroxyethylcellulose is commonly added following the citric acid charge and before the potassium hydroxide charge to ensure adequate dispersion and hydration. A hydration time of at least 30 minutes with mixing at elevated temperature (range about 140-150° F.) is often allowed to ensure physical stability of the final product.

The hydroxypropyl methyl cellulose thickener can be added in several ways. It can be dispersed in hot water of at least about 167° F., dispersed in a concentrated salt solution, dispersed in a premix of materials that do not contain water, or a combination of these methods. Once incorporated, hydroxypropyl methyl cellulose is best hydrated in cool water (range 68-77° F.). The material may be hydrated (30 min. to 1 hour) before addition of surfactants to ensure the final product is clear.

Benzalkonium chloride, as supplied, may contain small amounts of ethanol which positively impacts the solubility of the system as a whole. In some instances, it may be added after the batch is cool to avoid driving off the alcohol.

Phenoxyethanol, if used, is typically not be added to the batch until after the batch is cooled during polymer hydration.

Based on the components utilized and the general guidelines above for mixing various components, one skilled in the art would know and understand process parameters required to achieve a stable, homogeneous product.

EXAMPLES

Example 1—Antimicrobial Efficacy

Composition A provided in Table IA was evaluated for efficacy and compared to consumer grade antimicrobial handwashing compositions and routine handwashing soap without an antimicrobial. Initial testing was done comparing Composition A to two consumer grade handwashing soaps in an in vitro time kill test using a *Klebsiella pneumoniae* BAA-1705 strain that is a carbapenem resistant enterobacteriaceae. One of the consumer grade compositions comprised triclosan (0.15%) as the antimicrobial agent and the other benzalkonium chloride (0.13%). A routine handwash without an antimicrobial agent was used as a control. Results demonstrate that at 15, 30 and sixty seconds, Composition A ("EXP16003") was superior in log reduction (LR) of the microorganism when compared with consumer grade handwashing soaps (see FIG. 1 and Table IC).

TABLE IC

Antimicrobial Efficacy of Composition A Compared to Consumer Grade Handwashing Soaps

| | | *K. pneumoniae* BAA-1705 | | | |
|---|---|---|---|---|---|
| | | AVG LR* | | | base- |
| Product Name | | 15 s | 30 s | 60 s | line |
| Softsoap | Routine Handwash | 0.23 | 0.11 | −0.07 | 6.86 |
| Dial Gold Antibacterial Hand Soap with Moisturizer | Consumer Grade Triclosan Product (0.15%) | 0.25 | 0.06 | 0.08 | 6.86 |
| Softsoap Antibacterial Hand Soap with Moisturizers | Consumer Grade Benzalkonium chloride Product (0-13% BZK) | 0.14 | 0.37 | 1.33 | 6.86 |

TABLE IC-continued

Antimicrobial Efficacy of Composition A Compared to Consumer Grade Handwashing Soaps

|  |  | K. pneumoniae BAA-1705 | | | |
|---|---|---|---|---|---|
|  |  | AVG LR* | | | base- |
| Product Name |  | 15 s | 30 s | 60 s | line |
| EXP16003 BZK foam handwash | Professional Grade Benzalkonium chloride Product (0.5%) | 5.86 | 5.86 | 5.86 | 6.86 |

Figure 2:
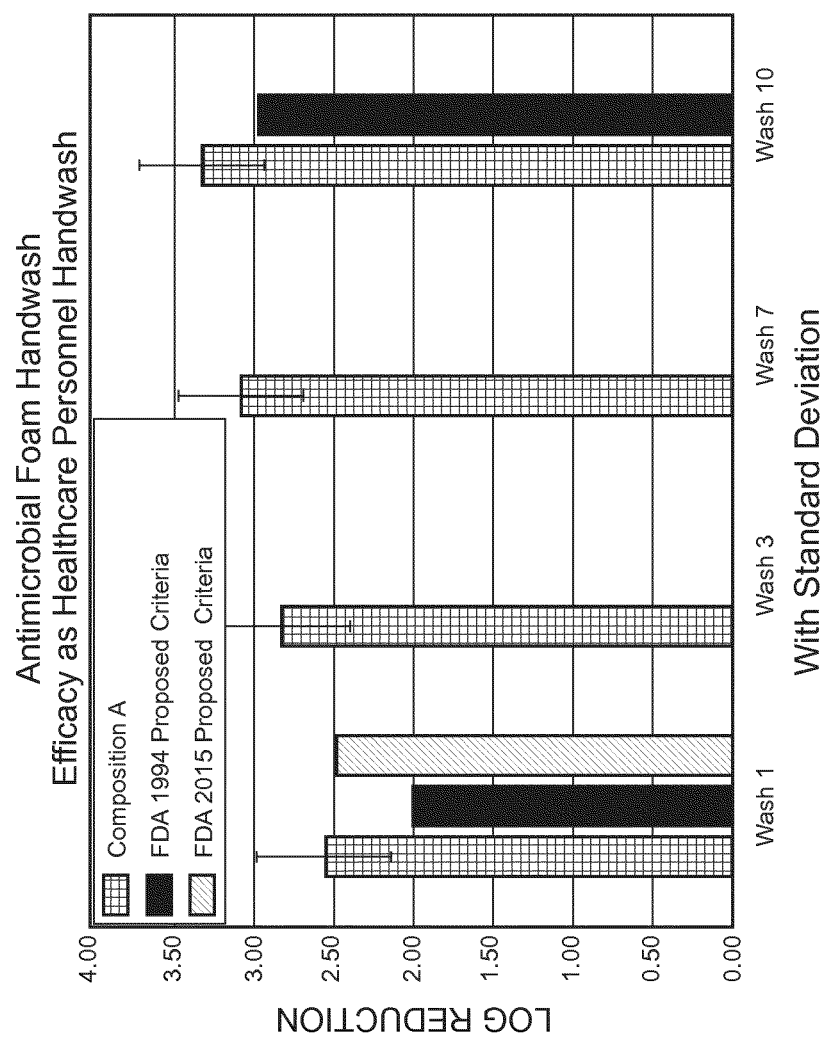
FIG. 2 is a bar graph comparing the efficacy of Composition A versus FDA criteria (log reduction) for Healthcare Personnel Antiseptic Drug Products at 1-wash and after repeated washings.

Additional testing was performed on Composition A to determine if FDA log reduction criteria for Healthcare Personnel Antiseptic Drug Products, Fed. Reg. 59 [116], June 1994; pp. 31402-31452, and the May 15, 2015 amendments thereto, are met. It was expected that the composition would be shown to be highly effective when tested according to standard test methods. FIG. 2 and Table ID (with standard deviation) shows that the antimicrobial composition exceeded FDA criteria (log reduction) at 1-wash and improved significantly over the course of several washings.

TABLE ID

FDA Proposed Criteria and Washings with Composition A

| Number of Washings | Composition A log reduction | FDA 1994 Proposed Criteria log reduction | FDA 1995 Proposed Criteria log reduction | Standard Deviation |
|---|---|---|---|---|
| Wash 1 | 2.57 | 2 | 2.5 | 0.4231 |
| Wash 3 | 2.85 |  |  | 0.4391 |
| Wash 7 | 3.10 |  |  | 0.39 |
| Wash 10 | 3.35 | 3 |  | 0.3832 |

Example 2—Mildness Testing

A Forearm Controlled Application Test (FCAT) was conducted to assess drying and conversely moisturization achieved by products on skin. In this test, products were applied to the volar (flat) part of the forearm. The surface area and flatness allowed for multiple products to be compared side by side with the skin serving as its own control. Typically, an untreated site and a water only site are used for controls. Assessments were made visually by trained evaluators and also by utilizing various instrument methods. The procedure entails: washing for 10 seconds, allowing product to sit for 90 seconds, rinsing and blotting. The procedure is repeated several times over five days. Analysis is conducted at various points, prior to each morning and at least three hours after the last applications. Statistical analysis of the data was then conducted.

A FCAT test comparing the Composition A and B to two competitive antimicrobial handwashing compositions revealed unexpected results for the composition. Results showed that the compositions had significantly better mildness as compared to the two competitive products.

Example 3—Skin Cleansing Without Dryness

Figure 3:
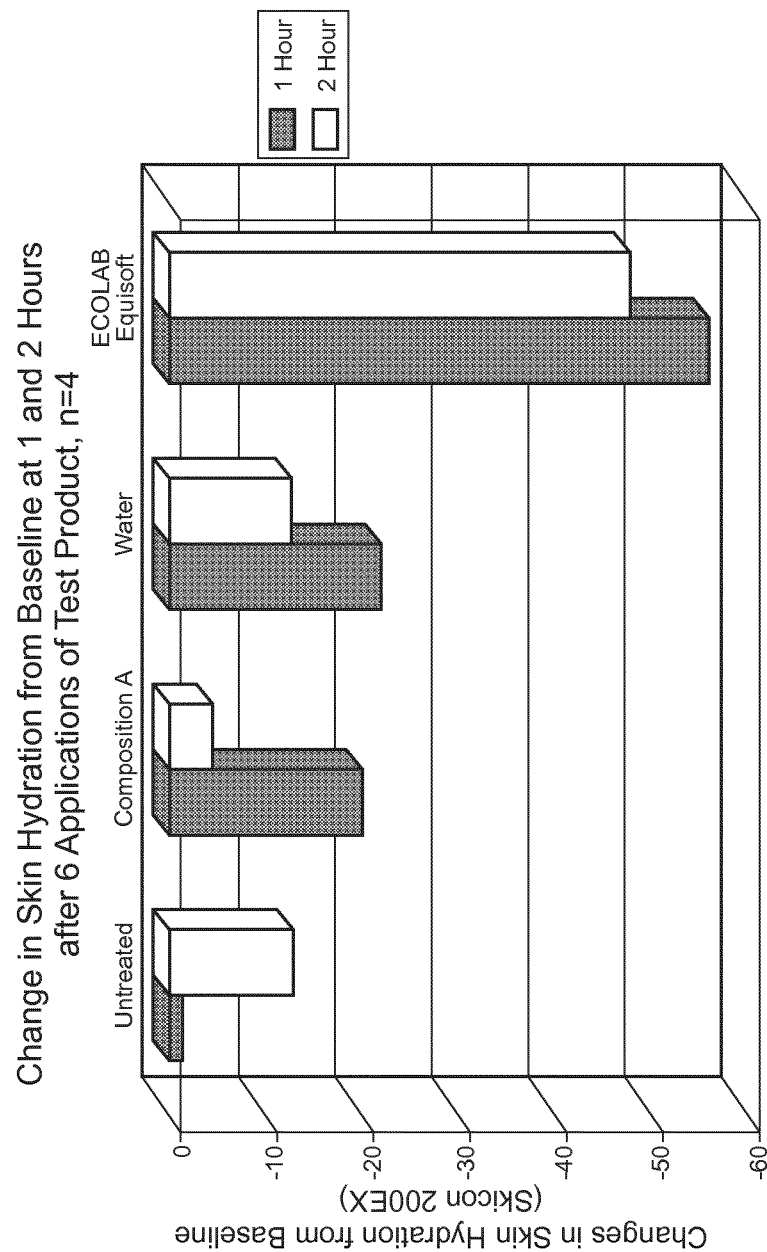
FIG. 3 is a bar graph comparing the changes in surface hydration from baseline for Composition A as compared to a water control, an untreated control and a commercial antimicrobial soap (ECOLAB Equi-Soft™ soap).

The Composition A was able to clean without drying the skin. This was demonstrated using a dermatological instrument known as the Skicon 200EX. This instrument consists of a probe with two electrodes. When the probe touches the skin, conductance between the two electrodes is detected as a change of voltage in the circuit and a value is displayed in micro-siemens (us). The moisture level of the skin is proportional to the conductance through the stratum corneum. FIG. 3 demonstrates the results obtained for the skin hydration of Composition A as compared to a competitive product (ECOLAB Equi-Soft), a water control, and an untreated control. The use of soyamidopropyl amine oxide contributed significantly to the non-drying cleansing profile as did the overall low surfactant levels and use of effective skin conditioners.

After skin hydration studies, the skin of one participant was photographed using a Visioscan. White lines in skin folds can be seen in Visioscan images when the skin is dry and damaged. Visioscan images demonstrated that Composition A is less drying than both water alone and the competitive product, leaving the skin almost as hydrated as an untreated control.

Example 4—Superior Efficacy at Lower Surfactant Levels

Figure 4:
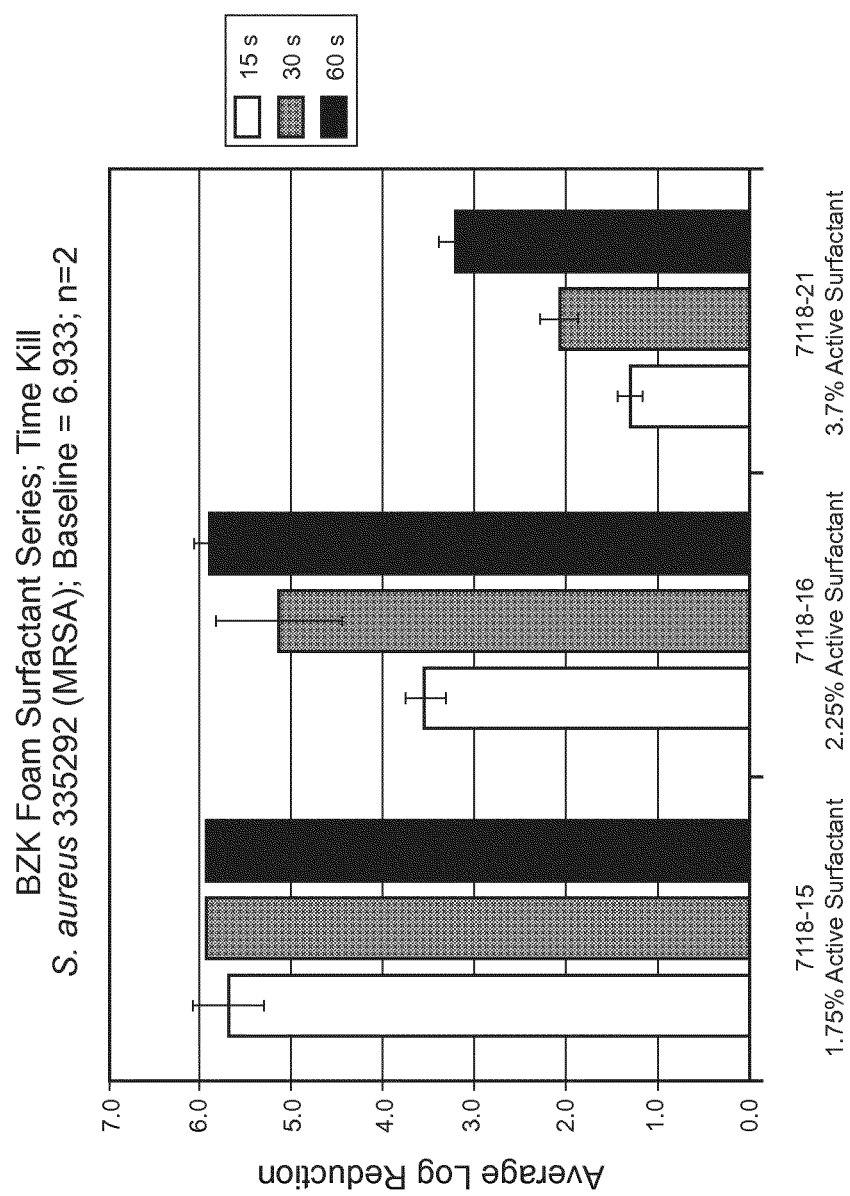
FIG. 4 is a bar graph showing the effect on the antimicrobial efficacy (average log reduction of *S. aureus* 33592 (MRSA)) of three prototype antimicrobial compositions sharing all the same ingredients and only differing in active surfactant concentration (ranging from 1.75 to 3.7% active surfactant).

It is speculated that the use of lower active surfactant levels allowed for the cationic active to be more bioavailable leading to enhanced microbial efficacy. FIG. 4 shows the impact of efficacy of lowering the active surfactant concentrations. Prototypes 7118-15, 7118-16 and 7118-21 shared all the same ingredients and only differed in the active surfactant concentrations; ranging from 3.7% active surfactant to 1.75% active surfactant. Lower levels of active surfactant unexpectedly achieved higher log reductions against S. aureus.

Figure 5:
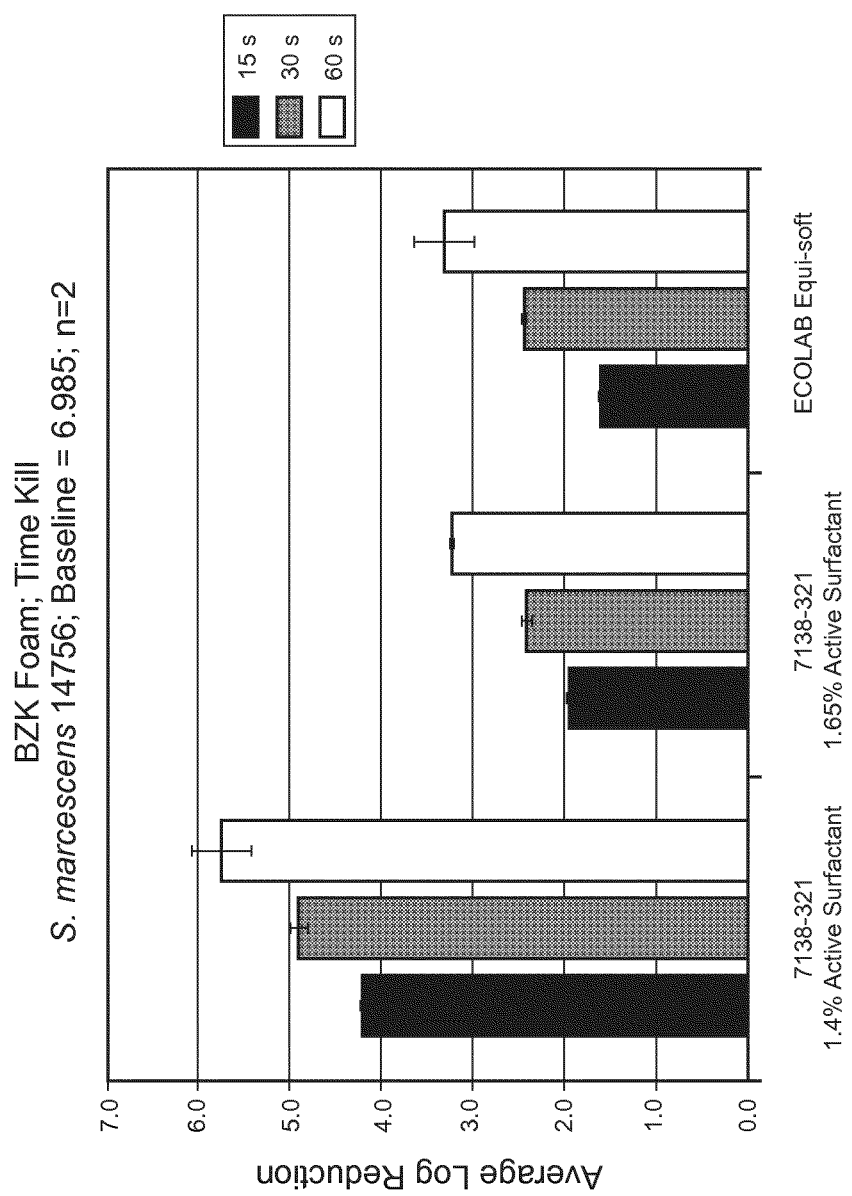
FIG. 5 is a bar graph showing the difference in efficacy achieved by two prototype antimicrobial compositions in comparison to a commercial antimicrobial soap (ECOLAB Equi-Soft™ soap); the prototype antimicrobial compositions shared all the same ingredients and only differed in the cocamidopropyl dimonium chloride phosphate concentration (1.40 wt % or 1.65 wt %).

It was also determined that more resistant organisms like S. marcescens required even lower active surfactant concentration in the compositions to allow the quaternary ammonium based phospholipid surfactant, cocamidopropyl dimonium chloride phosphate, to be sufficiently bioavailable to achieve the desired kill. FIG. 5 shows the difference in efficacy achieved by two Prototypes that shared all the same ingredients and only differed in the cocamidopropyl dimonium chloride phosphate concentration. From FIG. 5 it can be seen that 1.40 wt % cocamidopropyl dimonium chloride phosphate achieved significantly better microbial kill than 1.65 wt % cocamidopropyl dimonium chloride phosphate.

Example 5—Skin Conditioner Impact on Efficacy

Figure 6:
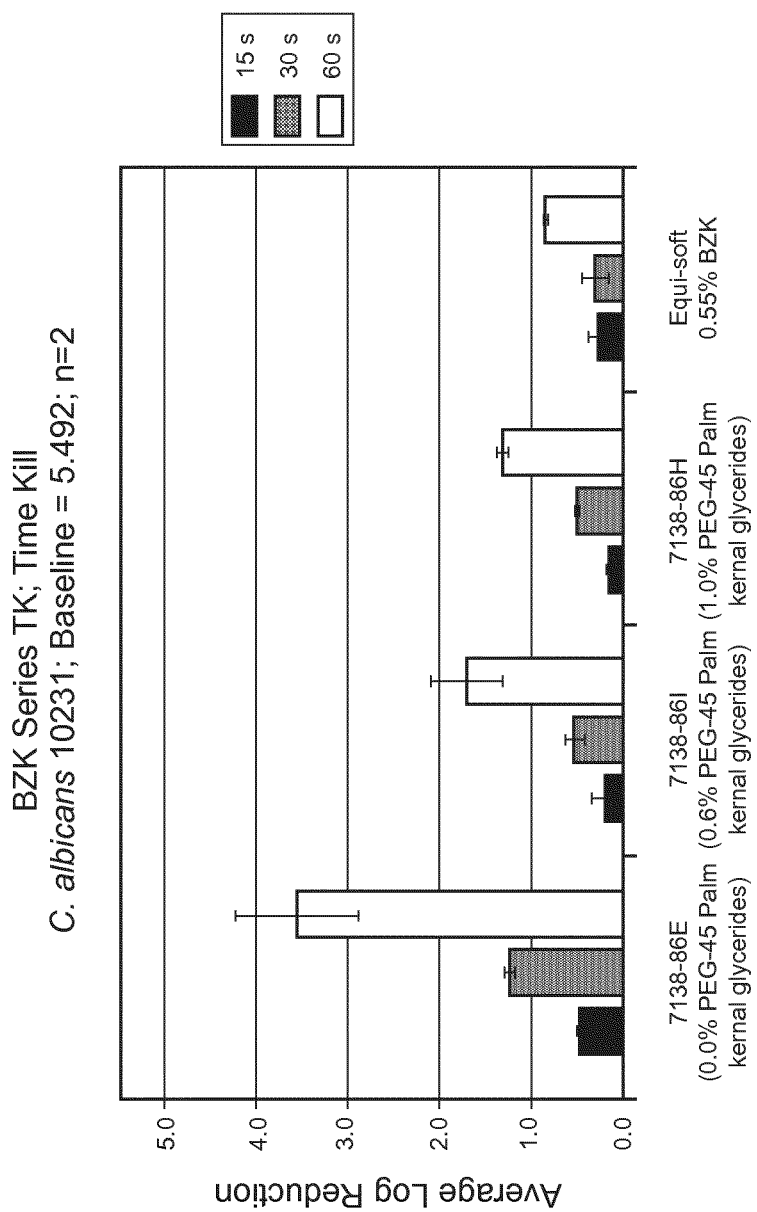
FIG. 6 is a bar graph showing the effect on the antimicrobial efficacy (average log reduction of *C. albicans* 10231) for three prototype antimicrobial compositions sharing all the same ingredients but differing in the amount of added PEG-45 palm kernel glycerides (ranging from 0 to 1.0%) in comparison to a commercial antimicrobial soap (ECOLAB Equi-Soft™ soap).

The efficacy of the composition was also enhanced by intentionally avoiding the use of skin conditioners that negatively impacted microbial efficacy. FIG. 6 shows the negative impact of PEG-45 palm kernel glycerides on the efficacy against C. albicans. Similar negative impacts on efficacy were noted with the use of PEG-6 caprylic/capric glycerides.

Example 6

A study was performed to evaluate the efficacy of Composition B comprising 0.7% benzalkonium chloride and a 4% chlorohexidine gluconate (CHG) handwash product, in a modified Health Care Personnel Handwash test. The study was based on the procedures described in the Tentative Final Monograph (TFM) [Vol. 59, No. 116, Jun. 17, 1994, FR 31402]. According to this modified procedure, a target was set to achieve 2 $\log_{10}$ reduction of the indicator organism Serratia marcescens (ATCC No. 14756) within 5 minutes after the first hand treatment and a 3 $\log_{10}$ reduction within 5 minutes after the tenth hand treatment.

The protocol used was based on a modified procedure adopted from the Tentative Final Monograph (TFM) [Vol. 59, No. 116, Jun. 17, 1994, FR 31402]. Deviations to the protocol were recorded (Appendix IV). The subjects were randomized using a blind draw of test articles.

Study Design and Procedure:

| Phase of Study | Procedure |
| --- | --- |
| Pre-Test Phase | Volunteers were screened and enrolled in the study as potential subjects. They were instructed to avoid contact with antimicrobials for the duration of the study. They were provided with a kit of non-antimicrobial personal care products. |
| Practice Inoculation | After a minimum of 5 days, during which the subjects avoided antimicrobials, they participated in a practice inoculation. Subjects used water to represent the inoculum. |
| Baseline Phase | A cleansing wash was performed. An estimate of the baseline population on the subjects' hands was determined. |
| Treatment Phase | Subjects were randomly assigned to one of the treatment groups. The subjects used the assigned product on inoculated hands. Sampling was performed after treatments 1, 3, 7 and 10. |

Plates with counts between 25 and 250 CFU were used. For dilution series where all plates were outside the 25-250 CFU range, the plate closest to 250 CFU was used. If two plates from the same dilution series both fell within the 25-250 CFU range, the lower CFU count was used regardless of dilution number. The average of duplicate plates was used to determine the count for each sample.

Raw data from baseline and post-treatment samples were converted into $\log_{10}$ values for each hand. The $\log_{10}$ reduction for each hand was calculated by subtracting the post-treatment value from the baseline value. The average of right and left hand values was used to determine the $\log_{10}$ recovery and $\log_{10}$ reduction from baseline for each subject at each sampling interval.

The paired difference between the post-treatment and baseline recovery values was calculated for each subject at each sampling interval for each test article. Statistical significance versus baseline was analyzed for the test product and the reference product at each time point using a paired t-test with 2-sided alpha=0.05.

Results and Discussion:

The raw data from the baseline and post-treatment counts was converted to $\log_{10}$ values for each hand. The $\log_{10}$ reduction values were calculated by subtracting the post-treatment $\log_{10}$ value from the baseline $\log_{10}$ value. The $\log_{10}$ reductions for the right and left hand were then averaged to get the average $\log_{10}$ reduction.

Figure 7:
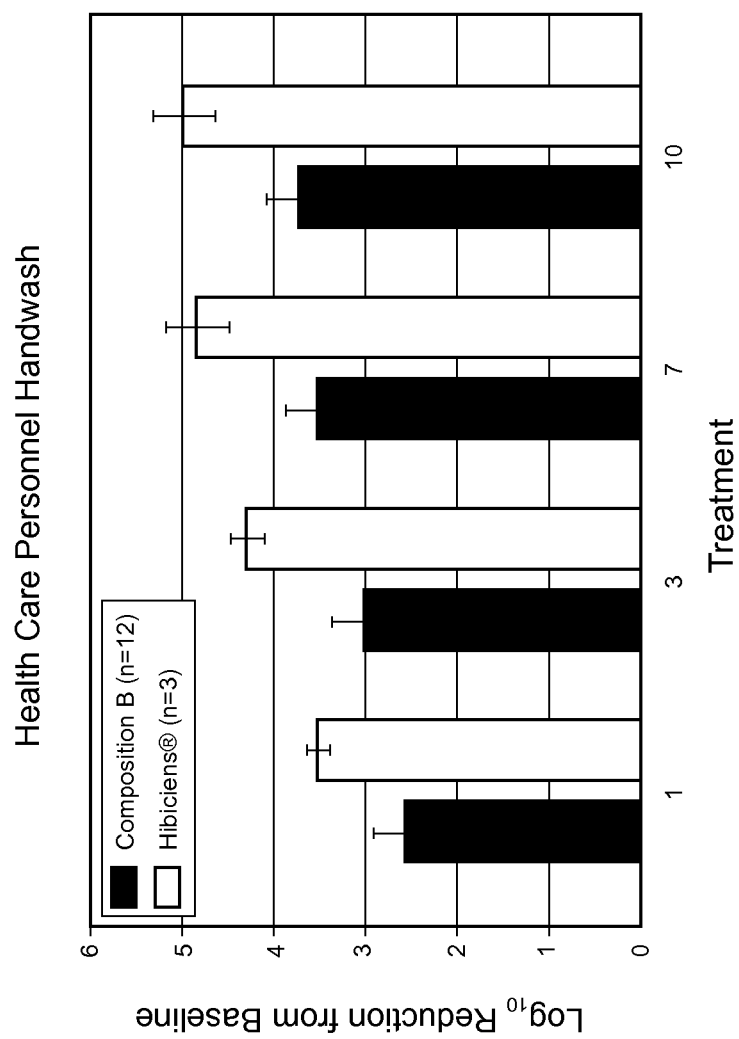
FIG. 7 is a bar graph showing the results of an evaluation of the efficacy of Composition B versus a 4% chlorohexidine gluconate handwash product (Hibiclens® liquid antimicrobial skin soap) in a modified Health Care Personnel Handwash test using *Serratia marcescens* (ATCC No. 14756) as the indicator organism.
Figure 8:
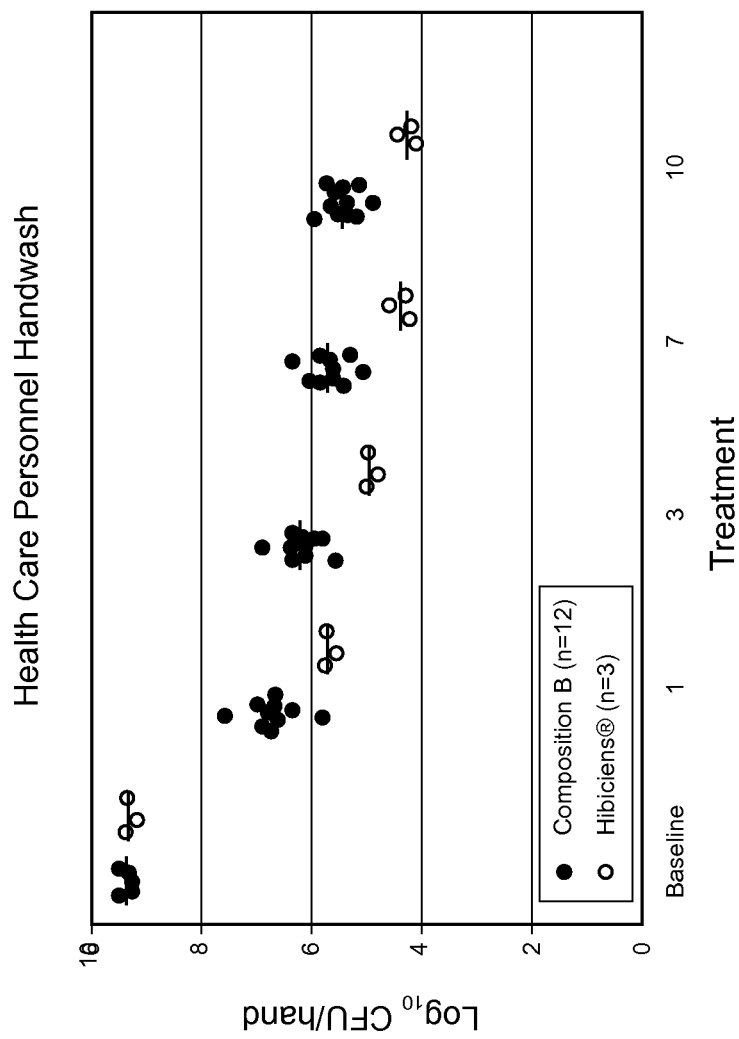
FIG. 8 is a graph showing the results in a modified Health Care Personnel Handwash test with *Serratia marcescens*

The results showed 91.67% (11/12) subjects using Composition B met the target performance criteria with an average $\log_{10}$ reduction of 2.58 after the first treatment and 3.83 after the tenth treatment (Table 2, FIG. 7). A paired t-test showed a statistically significant difference (p<0.0001) between the $\log_{10}$ recovery at baseline compared with recovery after treatment at each sampling interval (Table 3, FIG. 8). Additional statistical analysis was performed to determine the 95% confidence interval of the mean $\log_{10}$ reduction from baseline, which ranged from 2.35 to 2.82 after the first treatment and from 3.65 to 4.00 after the tenth treatment (Table 2).

The results showed 100% (3/3) subjects using the reference product, 4% CHG, met the target performance criteria with an average $\log_{10}$ reduction of 3.58 after the first treatment and 5.04 after the tenth treatment (Table 4, FIG. 7). A paired p-test showed a statistically significant difference (p-0.05) between the $\log_{10}$ recovery at baseline compared with recovery after treatment at each sampling interval (Table 5, FIG. 8). Additional statistical analysis was performed to determine the 95% confidence interval of the mean $\log_{10}$ reduction from baseline, which ranged from 3.35 to 3.80 after the first treatment and from 4.27 to 5.82 after the tenth treatment (Table 4).

TABLE 2

Composition B (0.7% BZK) $\log_{10}$ reduction from baseline
Composition B (n = 12)

| Subject | Treatment 1 | Treatment 3 | Treatment 7 | Treatment 10 |
| --- | --- | --- | --- | --- |
| 002 | 1.75 | 2.37 | 2.91 | 3.29 |
| 004 | 2.58 | 3.07 | 3.47 | 3.70 |
| 005 | 2.46 | 3.38 | 3.63 | 3.72 |
| 006 | 2.54 | 2.81 | 3.31 | 3.55 |
| 007 | 2.39 | 2.92 | 3.59 | 3.78 |
| 008 | 2.66 | 3.30 | 3.71 | 3.90 |
| 009 | 2.57 | 3.07 | 3.37 | 3.65 |
| 010 | 2.61 | 3.36 | 4.11 | 4.22 |
| 011 | 2.51 | 3.11 | 3.51 | 3.79 |
| 012 | 3.00 | 3.51 | 3.91 | 4.00 |
| 013 | 2.55 | 2.89 | 3.46 | 4.03 |
| 015 | 3.36 | 3.60 | 4.10 | 4.28 |
| Average | 2.58 | 3.12 | 3.59 | 3.83 |
| Standard Deviation | 0.37 | 0.34 | 0.34 | 0.28 |
| Standard Error | 0.11 | 0.10 | 0.10 | 0.08 |
| 95% Confidence Interval | 2.35 to 2.82 | 2.89 to 3.29 | 3.37 to 3.81 | 3.65 to 4.00 |
| Responder Rate (%) | 91.67 | N/A | N/A | 100.00 |

TABLE 3

Composition B (0.7% BZK) $\log_{10}$ Recovery
Composition B (n = 12)

| Subject | Baseline | Treatment 1 | Treatment 3 | Treatment 7 | Treatment 10 |
| --- | --- | --- | --- | --- | --- |
| 002 | 9.35 | 7.60 | 6.98 | 6.44 | 6.06 |
| 004 | 9.48 | 6.91 | 6.41 | 6.02 | 5.78 |
| 005 | 9.45 | 6.99 | 6.07 | 5.82 | 5.73 |
| 006 | 9.32 | 6.78 | 6.51 | 6.01 | 5.76 |
| 007 | 9.43 | 7.04 | 6.51 | 5.84 | 5.65 |
| 008 | 9.45 | 6.79 | 6.15 | 5.74 | 5.55 |
| 009 | 9.52 | 6.94 | 6.45 | 6.15 | 5.87 |
| 010 | 9.51 | 6.90 | 6.14 | 5.40 | 5.29 |
| 011 | 9.27 | 6.75 | 6.15 | 5.76 | 5.48 |
| 012 | 9.42 | 6.42 | 5.91 | 5.51 | 5.42 |
| 013 | 9.27 | 6.72 | 6.38 | 5.81 | 5.24 |
| 015 | 9.26 | 5.90 | 5.66 | 5.17 | 4.98 |
| Average | 9.39 | 6.81 | 6.28 | 5.81 | 5.57 |
| Standard Deviation | 0.95 | 0.40 | 0.34 | 0.34 | 0.30 |
| Standard Error | 0.28 | 0.11 | 0.10 | 0.10 | 0.09 |
| p-value vs. Baseline | — | <0.00001 | <0.00001 | <0.00001 | <0.00001 |

TABLE 4

Reference Product (Hibiclens ®, 4% CHG) $\log_{10}$ Reduction from Baseline
Hibiclens ® (n = 3)

| Subject | Treatment 1 | Treatment 3 | Treatment 7 | Treatment 10 |
| --- | --- | --- | --- | --- |
| 001 | 3.66 | 4.366 | 5.11 | 5.26 |
| 003 | 3.58 | 4.18 | 4.52 | 4.69 |

TABLE 4-continued

Reference Product (Hibiclens ®, 4% CHG) log₁₀ Reduction from Baseline Hibiclens ® (n = 3)

| Subject | Treatment 1 | Treatment 3 | Treatment 7 | Treatment 10 |
|---|---|---|---|---|
| 014 | 3.48 | 4.49 | 5.04 | 5.19 |
| Average | 3.58 | 4.34 | 4.89 | 5.04 |
| Standard Deviation | 0.09 | 0.15 | 0.32 | 0.31 |
| Standard Error | 0.05 | 0.09 | 0.19 | 0.18 |
| 95% Confidence Interval | 3.35 to 3.80 | 3.96 to 4.73 | 4.10 to 5.69 | 4.27 to 5.82 |
| Responder Rate (%) | 100.00 | N/A | N/A | 100.00 |

TABLE 5

Reference Product (Hibiclens ®, 4% CHG) log₁₀ Recovery Hibiclens ® (n = 3)

| Subject | Baseline | Treatment 1 | Treatment 3 | Treatment 7 | Treatment 10 |
|---|---|---|---|---|---|
| 001 | 9.49 | 5.83 | 5.13 | 4.38 | 4.24 |
| 003 | 9.21 | 5.63 | 5.03 | 4.69 | 4.53 |
| 014 | 9.35 | 5.87 | 4.86 | 4.31 | 4.16 |
| Average | 9.35 | 5.78 | 5.01 | 4.46 | 4.31 |
| Standard Deviation | 0.14 | 0.13 | 0.14 | 0.20 | 0.19 |
| Standard Error | 0.08 | 0.07 | 0.08 | 0.12 | 0.11 |
| p-value vs. Baseline | | 0.0002 | 0.0004 | 0.0014 | 0.0013 |

As seen from the results achieved, the target performance criteria set in this modified Health Care Personnel Handwash test, based on guidelines provided in the 1994 TFM, i.e., at least 2 log 10 reduction within 5 minutes after the first treatment and at least 3 log 10 reduction within 5 minutes after the tenth treatment, were met for both Composition B and the reference product (4% CHG).

Example 7—Antimicrobial Profile for Composition B

The Tentative Final Monograph for Healthcare Antiseptic Drug Products requires time kill studies to evaluate both the types of microorganisms that are susceptible to the product, and how rapidly the product acts against these microorganisms. The purpose of this study was to provide evidence for broad spectrum antimicrobial activity of this product and time kill data for technical literature. The efficacy of a 0.7% benzalkonium chloride (BZK) (Composition B) was evaluated against a broad spectrum of vegetative microorganisms. Composition B demonstrated rapid killing of the challenge organisms tested. The media and dilution fluid utilized are listed below:

Tryptic Soy Agar (TSA)
Sabouraud Dextrose Agar (SDA)
Letheen Agar
Letheen A/T (LAT) Agar
Tryptic Soy Agar with Sheep's Blood, Remel R01201
Chocolate Agar, Remel R01301
Butterfield's Buffer
TLSO
Letheen A/T (LAT) Broth
Microorganisms Utilized

| Organism | ATCC # or Clinical Isolate # | Additional Features |
|---|---|---|
| *Acinetobacter baumannii* | 19606 | Not applicable |
| *Acinetobacter baumannii* | BAA-1605 | Multi-drug resistant organism (MDRO) |
| *Acinetobacter lwoffii* | 15309 | Not applicable |
| *Bacteroides fragilis* | 234745 | Grow on TSA with Sheep's Blood in anaerobic container |
| *Candida albicans* | 10231 | Not applicable |
| *Candida tropicalis* | 13803 | Not applicable |
| *Corynebacterium diphtheria* | 13812 | Not applicable |
| *Enterobacter cloacae* | 13047 | Not applicable |
| *Enterococcus faecalis* | 29212 | Not applicable |
| *Enterococcus faecalis* | 51299 | Vancomycin-resistant *Enterococcus* (VRE) |
| *Enterococcus faecium* | 51559 | Vancomycin-resistant *Enterococcus* (VRE) |
| *Escherichia coli* | 8739 | Not applicable |
| *Escherichia coli* | 35150 | O157:h7 |
| *Haemophilus influenza* | 10211 | Grow on Chocolate Agar |
| *Klebsiella pneumoniae* | 4352 | Not applicable |
| *Klebsiella pneumoniae* | BAA-1705 | Carbapenem-resistant Enterobacteriaceae (CRE, KPB) |
| *Klebsiella pneumoniae* | BAA-2146 | Carbapenem-resistant Enterobacteriaceae (CRE, NDM-1) |
| *Klebsiella oxytoca* | 8724 | Not applicable |
| *Micrococcus luteus* | 7468 | Now known as *M. yunnanensis* |
| *Proteus mirabilis* | 7002 | Not applicable |
| *Pseudomonas aeruginosa* | 15442 | Not applicable |
| *Salmonella enterica* | 10708 | Not applicable |
| *Serratia marcescens* | 14756 | Not applicable |
| *Shigella dysenteriae* | 13313 | Not applicable |
| *Staphylococcus aureus* | 6538 | Not applicable |
| *Staphylococcus aureus* | 33591 | Methicillin-resistant *Staphylococcus aureus* (MRSA) |
| *Staphylococcus aureus* | 33592 | Methicillin-resistant *Staphylococcus aureus* (MRSA) |
| *Staphylococcus aureus* | CV573 (USA300) | Community-associated Methicillin-resistant *Staphylococcus aureus* (CA-MRSA) |
| *Staphylococcus epidermidis* | 12228 | Not applicable |
| *Staphylococcus haemolyticus* | 29970 | Not applicable |

| Organism | ATCC # or Clinical Isolate # | Additional Features |
|---|---|---|
| Staphylococcus hominis | 27844 | Not applicable |
| Staphylococcus saprophyticus | 35552 | Not applicable |
| Streptococcus pneumoniae | 6303 | Grow on TSA with Sheep's Blood |
| Streptococcus pyogenes | 19615 | Not applicable |

Methods

Inoculum Preparation:

Working cultures of the listed organisms were started from stocks onto the appropriate growth media. Yeast were grown on Sabouraud Dextrose Agar (SDA). Bacteria were grown on Tryptic Soy Agar (TSA) with the exception of *H. influenza*, which was grown on Chocolate Agar, *S. pneumoniae*, grown on TSA with Sheep's Blood, and *B. fragilis*, which was grown on TSA with Sheep's Blood in an anaerobic container. The cultures were incubated at the appropriate temperature for 24±4 hours before testing.

Immediately before testing, a sterile cotton swab was used to re-suspend the microorganisms in sterile Butterfield's Buffer to obtain a microbial suspension with a titer of approximately $1 \times 10^9$ colony forming units (CFU)/mL.

Neutralizer Confirmation Procedure

A neutralization assay was conducted based, in part, on a modification of ASTM E1054-08. Briefly, 9.0 mL of TLSO broth was inoculated with 0.1 mL of *Serratia marcescens* ATCC #14756 or *Staphylococcus aureus* ATCC #6538 suspension containing approximately $1 \times 10^4$ CFU/mL. The mixture was vortexed and 1.0 mL of test product was added immediately. After 15 seconds and 30 minutes, a 1 mL sample of this mixture was plated in Letheen A/T agar.

After incubation, the plates were counted and CFU transformed to $\log_{10}$ for analysis. The results were compared to control samples without test product and the inactivating effect (IE) was calculated. The IE for each organism was ≥0.8, meeting the criteria for neutralizer suitability. Furthermore, by comparing $\log_{10}$ CFU of each organism exposed to neutralizers versus buffer alone, the neutralizers were determined to be toxic. These challenge organisms were assumed to be representative of the other organisms used in this study, and the neutralizer system was deemed effective.

Sample Preparation

Straight-side wide-mouth Nalgene jars were filled with 9.9 mL of test product. Test samples and baseline samples were analyzed in duplicate.

Efficacy Test Procedure

The time kill method was performed. A 0.1 mL aliquot of the microorganism suspension was added to ajar containing 9.9 mL of the test product. At time points of 15, 30 and 60 seconds post-inoculation, a 1.0 mL sample was aseptically removed and transferred to a tube containing 9.0 mL of TLSO for neutralization. Serial dilutions were performed in Letheen A/T (LAT) broth and 1 mL samples were plated in Letheen A/T (LAT) Agar for bacteria, or SDA for yeast. Due to the growth requirements of the test organisms, *H. influenza* dilutions were spread-plated on Chocolate Agar, and *S. pneumoniae* and *B. fragilis* dilutions were spread plated on TSA with Sheep's Blood.

Baseline samples were prepared in a similar manner using sterile Butterfield's Buffer in place of test product. Serial dilutions were performed in Letheen A/T (LAT) broth and 1.0 mL samples were plated in Letheen A/T (LAT) agar for bacteria and SDA for yeast. For *H. influenza, S. pneumoniae*, and *B. fragilis*, 0.1 mL samples were spread plated on Chocolate Agar or TSA with Sheep's Blood as described for the test samples.

Plates were incubated at the appropriate temperature for 48±4 hours, with the exception of *S. marcescens*, which was incubated for 24±4 hours. The *B. fragilis* plates were incubated in an anaerobic container. The number of viable organisms per mL of sample was determined by standard plate count and transformed to $\log_{10}$ values for analysis.

Results

The average log reduction from baseline for each test organism is shown for Composition B in Tables 6-8. A complete kill with a lower limit of detection of 10 CFU/mL was observed for all of the challenge organisms, as indicated by the ">" symbol.

TABLE 6

Efficacy of Composition B against yeast using a time kill method.

| Test Organism | ATCC# | $\log_{10}$ Inoculum | Average Log Reduction | | | Percent Kill | | |
|---|---|---|---|---|---|---|---|---|
| | | | 15 s | 30 s | 60 s | 15 s | 30 s | 60 s |
| Candida albicans | 10231 | 6.228 | 2.611 | 4.328 | 5.228 | 99.7549 | 99.9953 | >99.999 |
| Candida tropicalis | 13803 | 6.086 | 4.634 | 5.086 | 5.086 | 99.9977 | >99.999 | >99.999 |

TABLE 7

Efficacy of Composition B against gram-negative bacteria using a time kill method.

| Test Organism | ATCC# | $\log_{10}$ Inoculum | Average Log Reduction | | | Percent Kill | | |
|---|---|---|---|---|---|---|---|---|
| | | | 15 s | 30 s | 60 s | 15 s | 30 s | 60 s |
| Acinetobacter baumannii | 19606 | 6.975 | 5.975 | 5.975 | 5.975 | >99.999 | >99.999 | >99.999 |
| Acinetobacter baumannii (MDRO) | BAA-1605 | 6.694 | 5.694 | 5.694 | 5.694 | >99.999 | >99.999 | >99.999 |
| Acinetobacter lwoffii | 15309 | 6.538 | 5.538 | 5.538 | 5.538 | >99.999 | >99.999 | >99.999 |

TABLE 7-continued

Efficacy of Composition B against gram-negative bacteria using a time kill method.

| Test Organism | ATCC# | Log₁₀ Inoculum | Average Log Reduction | | | Percent Kill | | |
|---|---|---|---|---|---|---|---|---|
| | | | 15 s | 30 s | 60 s | 15 s | 30 s | 60 s |
| *Bacteroides fragilis* | 23745 | 6.189 | 5.189 | 5.189 | 5.189 | >99.999 | >99.999 | >99.999 |
| *Enterobacter cloacae* | 13047 | 6.919 | 5.919 | 5.919 | 5.919 | >99.999 | >99.999 | >99.999 |
| *Escherichia coli* | 8739 | 6.924 | 5.924 | 5.924 | 5.924 | >99.999 | >99.999 | >99.999 |
| *Escherichia coli* O157:H7 | 35150 | 6.752 | 5.752 | 5.752 | 5.752 | >99.999 | >99.999 | >99.999 |
| *Haemophilus influenzae* | 10211 | 6.146 | 5.146 | 5.146 | 5.146 | >99.999 | >99.999 | >99.999 |
| *Klebsiella oxytoca* | 8724 | 6.922 | 5.922 | 5.922 | 5.922 | >99.999 | >99.999 | >99.999 |
| *Klebsiella pneumoniae* | 4352 | 6.973 | 5.973 | 5.973 | 5.973 | >99.999 | >99.999 | >99.999 |
| *Klebsiella pneumoniae* (CRE, KPC) | BAA-1705 | 6.848 | 5.848 | 5.848 | 5.848 | >99.999 | >99.999 | >99.999 |
| *Klebsiella pneumoniae* (CRE, NDM-1) | BAA-2146 | 6.803 | 5.803 | 5.803 | 5.803 | >99.999 | >99.999 | >99.999 |
| *Proteus mirabilis* | 7002 | 7.037 | 6.037 | 6.037 | 6.037 | >99.9999 | >99.9999 | >99.9999 |
| *Pseudomonas aeruginosa* | 15442 | 6.932 | 5.932 | 5.932 | 5.932 | >99.999 | >99.999 | >99.999 |
| *Salmonella enterica* | 10708 | 6.922 | 5.922 | 5.922 | 5.922 | >99.999 | >99.999 | >99.999 |
| *Serratia marcescens* | 14756 | 7.019 | 6.019 | 6.019 | 6.019 | >99.9999 | >99.9999 | >99.9999 |
| *Shigella dysenteriae* | 13313 | 6.906 | 5.906 | 5.906 | 5.906 | >99.999 | >99.999 | >99.999 |

TABLE 8

Efficacy of Composition B against gram-positive bacteria using a kill method

| Test Organism | ATCC# | Log₁₀ Inoculum | Average Log Reduction | | | Percent Kill | | |
|---|---|---|---|---|---|---|---|---|
| | | | 15 s | 30 s | 60 s | 15 s | 30 s | 60 s |
| *Corynabacterium diphtheriae* | 13812 | 6.949 | 5.949 | 5.949 | 5.949 | >99.999 | >99.999 | >99.999 |
| *Enterococcus faecalis* | 29212 | 6.948 | 5.948 | 5.948 | 5.948 | >99.999 | >99.999 | >99.999 |
| *Enterococcus faecalis* (VRE) | 51299 | 6.898 | 5.898 | 5.898 | 5.898 | >99.999 | >99.999 | >99.999 |
| *Enterococcus faecium* (VRE) | 51559 | 6.714 | 5.714 | 5.714 | 5.714 | >99.999 | >99.999 | >99.999 |
| *Micrococcus yunnanensis* (formerly *M. luteus*) | 7468 | 6.484 | 5.484 | 5.484 | 5.484 | >99.999 | >99.999 | >99.999 |
| *Staphylococcus aureus* | 6538 | 6.690 | 5.690 | 5.690 | 5.690 | >99.999 | >99.999 | >99.999 |
| *Staphylococcus aureus* (MRSA) | 33591 | 6.672 | 5.672 | 5.672 | 5.672 | >99.999 | >99.999 | >99.999 |
| *Staphylococcus aureus* (MRSA) | 33592 | 6.961 | 5.961 | 5.961 | 5.961 | >99.999 | >99.999 | >99.999 |
| *Staphylococcus aureus* (CA-MRSA) | CV573 (USA300) | 7.023 | 6.023 | 6.023 | 6.023 | >99.9999 | >99.9999 | >99.9999 |
| *Staphylococcus epidermidis* | 12228 | 6.572 | 5.572 | 5.572 | 5.572 | >99.999 | >99.999 | >99.999 |
| *Staphylococcus haemolyticus* | 29970 | 6.832 | 5.832 | 5.832 | 5.832 | >99.999 | >99.999 | >99.999 |
| *Staphylococcus hominis* | 27844 | 6.961 | 5.961 | 5.961 | 5.961 | >99.999 | >99.999 | >99.999 |
| *Staphylococcus saprophyticus* | 35552 | 6.698 | 5.961 | 5.961 | 5.961 | >99.999 | >99.999 | >99.999 |
| *Streptococcus pneumoniae* | 6303 | 6.911 | 5.911 | 5.911 | 5.911 | >99.999 | >99.999 | >99.999 |
| *Streptococcus pyogenes* | 19615 | 6.973 | 5.973 | 5.973 | 5.973 | >99.999 | >99.999 | >99.999 |

CONCLUSION

These results demonstrated that Composition B with 0.7% benzalkonium chloride, has fast-acting antimicrobial efficacy against a broad spectrum of vegetative microorganisms when tested.

Illustrative Embodiments

Reference is made in the following to a number of illustrative embodiments of the subject matter described herein. The following embodiments describe illustrative embodiments that may include various features, characteristics, and advantages of the subject matter as presently described. Accordingly, the following embodiments should not be considered as being comprehensive of all of the possible embodiments or otherwise limit the scope of the compositions described herein.

In one aspect, the foaming, antimicrobial compositions may include: a cationic antimicrobial component; a surfactant combination comprising two or more tertiary amine oxide surfactants, alkyl glycoside and/or PEG-based nonionic surfactant, and zwitterionic surfactant; skin conditioning agent; foam stabilizer; and water. Such compositions may also include one or more of the following: after-feel component, additional antimicrobial, solvent, viscosity modifying agent, preservative, perfume, dye, and buffer. In some embodiments, the skin conditioning agent may include humectant, emollient, cationic surfactant different from and in addition to that comprising the surfactant combination, nonionic polymer, and/or cationic polymer. In some embodiments, the zwitterionic surfactant may include a quaternary ammonium phospholipid. For example, the antimicrobial composition may include: about 0.3 to 1.0 wt. % of the cationic antimicrobial component; no more than about 5 wt. % of the surfactant combination; about 0.5 to 2 wt. % of the skin conditioning agent; about 0.25 to 2 wt. % of the foam stabilizer; and at least about 75 wt. % water. In some embodiments, the combined amount of the tertiary amine oxide surfactants, the isopropanolamide, the zwitterionic surfactant and the alkyl glycoside and/or PEG-based nonionic surfactant may constitute no more than about 2.5 wt. %, no more than about 2.0 wt. % and, desirably, no more than about 1.7 wt. % of the composition. In some embodiments, the composition may further include one or more of after-feel component, additional antimicrobial, solvent, viscosity modifying agent, preservative, perfume, dye, and buffer. In some embodiments, such compositions may be substantially free of PEG fatty acid glycerides, such as PEG-45 palm kernel glycerides and PEG-6 caprylic/capric glycerides, i.e., contain less than 0.1 wt. % PEG fatty acid glycerides.

In one aspect, the foaming, antimicrobial composition may include about 0.3 to 1.0 wt. % antimicrobial benzyl quaternary ammonium salt; about 0.5 to 3 wt. % tertiary amine oxide surfactant, which includes tertiary fatty amine oxide and fatty acid amidoalkyl tertiary amine oxide; about 0.2 to 1 wt. % alkyl glycoside; about 0.05 to 0.5 wt. % $C_{10}$-$C_{16}$ fatty acid isopropanolamide; about 0.05 to 0.3 wt. % quaternary ammonium phospholipid zwitterionic surfactant; about 0.5 to 2 wt. % water-soluble polyethyleneglycol polysiloxane; about 0.5 to 2 wt. % PEG-based nonionic polymer; about 1 to 5 wt. % humectant; and at least about 80 wt % water. In such compositions, the combined amount of the tertiary amine oxide surfactants, the isopropanolamide, the zwitterionic surfactant and the alkyl glycoside may desirably constitute no more than about 2.5 wt. %, no more than about 2.0 wt. % and, often, no more than about 1.7 wt. % of the composition.

In some embodiments, the composition may include: about 0.3 to 1 wt. % of the cationic antimicrobial component; about 0.5 to 3 wt. % of the two or more tertiary amine oxide surfactants; about 0.2 to 4 wt. % of the alkyl glycoside and/or PEG-based nonionic surfactant; about 0.05 to 0.3 wt. % of the zwitterionic surfactant; about 0.05 to 0.5 wt. % of the fatty acid isopropanolamide, which comprises $C_{10}$-$C_{16}$ fatty acid isopropanolamide; about 0.5 to 2 wt. % of the silicone-based skin conditioning agent. The composition may also include about 1 to 15 wt. % polyol humectant; about 0.1 to 2 wt. % of a cellulose derivative; and/or about 0.05 to 1 wt. % preservative. In some embodiments, the composition may further include a polycationic polymer, such as an acrylamide-based cationic copolymer, and/or a nonionic polymer, such as a PEG-based nonionic polymer, e.g., a polymeric polyethyleneglycol fatty acid diester. In some embodiments, the composition may further include a cellulose derivative. In some embodiments, the composition may further include a preservative. In some embodiments, the composition may further include alkyl polyglycoside surfactant. In some embodiments, the composition may further include citrate buffer. In some embodiments, the cationic antimicrobial agent may include benzyl quaternary ammonium salt, such as benzalkonium chloride.

In some embodiments, the two or more tertiary amine oxide surfactants may include tertiary fatty amine oxide and fatty acid amidoalkyl tertiary amine oxide; the skin conditioning agent may include a silicone-based skin conditioning agent; the composition may include at least about 75 wt. % water; and further include fatty acid isopropanolamide and a polyol humectant. In some embodiments, the cationic antimicrobial component may include benzalkonium chloride; the two or more tertiary amine oxide surfactants may include lauramine oxide, soyamidopropyl amine oxide, and/or cocamidopropyl amine oxide; the PEG-based nonionic surfactant may include polyethyleneglycol sorbitan fatty acid ester, such as PEG-80 sorbitan laurate; the zwitterionic surfactant may include cocamidopropyl PG-dimonium chloride phosphate; the fatty acid isopropanolamide may include $C_{10}$-$C_{16}$ fatty acid isopropanolamide; the silicone-based skin conditioning agent may include polyethyleneglycol polysiloxane; the polyol humectant may include glycerin, sorbitol, and/or hexylene glycol; and the composition further include a cellulose derivative and preservative. In some embodiments, the composition may include: about 0.3 to 1 wt. % of the cationic antimicrobial component; about 0.5 to 3 wt. % of the two or more tertiary amine oxide surfactants; about 0.5 to 4 wt. % of the PEG-based nonionic surfactant; about 0.05 to 0.5 wt. % of the zwitterionic surfactant; about 0.05 to 0.5 wt. % of the fatty acid isopropanolamide, which includes $C_{10}$-$C_{16}$ fatty acid isopropanolamide; and about 0.5 to 2 wt. % of the silicone-based skin conditioning agent. The composition may further include about 1 to 15 wt. % polyol humectant; about 0.1 to 2 wt. % of a cellulose derivative; and about 0.05 to 1 wt. % preservative.

In one aspect, the present technology provides an antimicrobial composition that includes: a cationic antimicrobial component; tertiary amine oxide surfactant including a tertiary fatty amine oxide and a fatty acid amidoalkyl tertiary amine oxide; a PEG-based nonionic surfactant; a $C_{10}$-$C_{16}$ fatty acid isopropanolamide; a water-soluble silicone polymer; humectant; and at least about 75 wt % water. In some embodiments, the cationic antimicrobial component may include benzyl quaternary ammonium antimicrobial. Preferably, the benzyl quaternary ammonium antimicrobial includes alkyldimethylbenzylammonium chloride. In some embodiments, the tertiary fatty acid amidoalkyl tertiary amine oxide may include one or more of soyamidopropyl amine oxide and cocamidopropyl amine oxide. Preferably, the tertiary fatty amine oxide includes lauryl amine oxide. In some embodiments, the PEG-based nonionic surfactant may include one or more of polyethyleneglycol fatty acid diester and polyethyleneglycol sorbitan fatty acid ester. In some embodiments, the $C_{10}$-$C_{16}$ fatty acid isopropanolamide may include cocamide monoisopropanolamide. In some embodiments, the water-soluble silicone polymer may include polyethyleneglycol dimethicone. In some embodiments, the humectant may include one or more of hexylene glycol, glycerin, and sorbitol. In some embodiments, the composition may include: about 0.3 to 1.0 wt. % of the cationic antimicrobial component; about 0.5 to 2 wt. % of the tertiary amine oxide surfactant; about 0.5 to 2.5 wt. % of the PEG-based nonionic surfactant; about 0.05 to about 0.5 wt. % of the $C_{10}$-$C_{16}$ fatty acid isopropanolamide; about 0.5 to 2 wt. % of the water-soluble silicone polymer; about 1 to 15 wt. % humectant; and at least about 75 wt. % water. In some embodiments, the cationic antimicrobial component may include a benzalkonium antimicrobial; the tertiary fatty amine oxide may include lauryl amine oxide and the fatty acid amidoalkyl tertiary amine oxide may include one or more of soyamidopropyl amine oxide and cocamidopropyl amine oxide; the PEG-based nonionic surfactant may include one or more of a polyethyleneglycol fatty acid diester and a polyethyleneglycol sorbitan fatty acid ester; the $C_{10}$-$C_{16}$ fatty acid isopropanolamide may include cocamide monoisopropanolamide; the water-soluble silicone polymer may include polyethyleneglycol dimethicone; and the humectant may include one or more of hexylene glycol, glycerin, and sorbitol. Preferably, the cationic antimicrobial component includes alkyldimethylbenzylammonium chloride; the tertiary fatty amine oxide includes lauryl amine oxide and the fatty acid amidoalkyl tertiary amine oxide includes one or more of soyamidopropyl amine oxide and cocamidopropyl amine oxide; the PEG-based nonionic surfactant includes one or more of polyethyleneglycol distearate and polyethyleneglycol sorbitan laurate; the $C_{10}$-$C_{16}$ fatty acid isopropanolamide includes cocamide monoisopropanolamide; the water-soluble silicone polymer includes polyethyleneglycol dimethicone; and the humectant includes one or more of hexylene glycol, glycerin, and sorbitol.

The composition may further include one or more of the following: alkyl glycoside, cellulose derivative, cationic acrylamide based polymer, buffer, pH adjustor, and preservative. In some embodiments, the composition includes the quaternary ammonium phospholipid. Preferably, the quaternary ammonium phospholipid includes cocamidopropyl PG-dimonium chloride phosphate. In some embodiments, the composition includes the alkyl glycoside. Desirably, the alkyl glycoside includes decyl glucoside. In some embodiments, the composition includes the cellulose derivative. Preferably, the cellulose derivative includes one or more of cetyl hydroxyethylcellulose and hydroxypropyl methylcellulose. In some embodiments, the composition includes the cationic acrylamide based polymer. Desirably, the cationic acrylamide based polymer includes an acrylamide/diallyldimethylammonium chloride copolymer. In some embodiments, the composition includes the buffer, which includes a carboxylic acid and a salt thereof. In some embodiments, the buffer may be a citrate buffer. In some embodiments, the composition includes the pH adjuster, which includes a base. Commonly, the base may include potassium hydroxide and/or sodium hydroxide. In some embodiments, the composition includes the preservative. Desirably, the preservative includes phenoxyethanol. In some embodiments, the composition may include: h. about 0.25 to 1 wt. % alkyl glycoside; i. about 0.1 to 2 wt. % cellulose derivative; j. about 0.05 to 0.3 wt. % cationic acrylamide based polymer; k. about 0.01 to 0.1 wt. % buffer; and l. about 0.05 to 1 wt. % preservative.

In some instances, the composition includes: about 0.3 to 1.0 wt. % of the cationic antimicrobial component, which includes alkyldimethylbenzylammonium chloride; about 0.5 to 2 wt. % of the tertiary amine oxide surfactant, which includes lauryl amine oxide, soyamidopropyl amine oxide, and cocamidopropyl amine oxide; about 0.5 to 2 wt. % of the PEG-based nonionic surfactant, which includes polyethyleneglycol distearate; about 0.1 to 0.3 wt. % of the $C_{10}$-$C_{16}$ fatty acid isopropanolamide, which includes cocamide monoisopropanolamide; about 0.5 to 2 wt. % of the water-soluble silicone polymer, which includes polyethyleneglycol dimethicone; and about 1 to 12 wt. % of the humectant, which includes hexylene glycol, glycerin, and sorbitol. In some embodiments, the composition also includes: about 0.25 to 1 wt. % decyl glucoside; about 0.1 to 2 wt. % cetyl hydroxyethylcellulose; about 0.05 to 0.2 wt. % acrylamide/diallyldimethylammonium chloride copolymer; about 0.01 to 0.1 wt. % of a buffer; and/or about 0.05 to 1 wt. % phenoxyethanol.

In one aspect, the present technology provides an antimicrobial composition including: a. about 0.3 to 1.0 wt. % antimicrobial benzyl quaternary ammonium salt; b. about 0.5 to 2 wt. % tertiary amine oxide surfactant, which includes $C_{10}$-$C_{16}$ fatty amine oxide and $C_{10}$-$C_{18}$ fatty acid amidopropyl amine oxide; c. about 0.5 to 4 wt. % PEG-based nonionic surfactant, which includes polyethyleneglycol fatty acid diester; d. about 0.05 to 0.5 wt. % $C_{10}$-$C_{16}$-fatty acid isopropanolamide; e. about 0.05 to 0.3 wt. % zwitterionic surfactant, which includes fatty amidopropyl PG-dimonium chloride phosphate; f. about 1 to 10 wt. % polyol humectant, which includes glycerin, sorbitol and/or hexylene glycol; g. about 0.1 to 1 wt. % cellulose derivative; h. about 0.1 to 1 wt. % preservative; i. about 0.5 to 2 wt. % silicone-based skin conditioning agent, which includes polyethyleneglycol dimethicone; and j. at least about 75 wt. % water.

In some embodiments, the present technology provides an antimicrobial composition that includes: a. about 0.3 to 0.8 wt. % benzalkonium chloride; about 0.5 to 1.5 wt. % tertiary amine oxide surfactant, which includes lauramine oxide, soyamidopropyl amine oxide, and cocamidopropyl amine oxide; about 0.2 to 1 wt. % alkyl glycoside, which includes decyl glucoside; about 0.5 to 2 wt. % PEG-based nonionic polymer, which includes polymeric polyethyleneglycol distearate; about 0.05 to 0.5 wt. % $C_{10}$-$C_{16}$-fatty acid isopropanolamide; about 0.05 to 0.3 wt. % zwitterionic surfactant, which includes cocamidopropyl PG-dimonium chloride phosphate; about 5 to 12 wt. % polyol humectant, which includes glycerin, sorbitol and/or hexylene glycol; about 0.1 to 1 wt. % cellulose derivative; about 0.1 to 1 wt. % preservative, which includes phenoxyethanol; about 0.5 to 2 wt. % silicone-based skin conditioning agent, which includes PEG-8 dimethicone; and at least about 80 wt. % water.

In some embodiments, the present technology provides an antimicrobial composition that includes: a. about 0.3 to 1.0 wt. % benzalkonium chloride; about 0.5 to 2 wt. % tertiary amine oxide surfactant, which includes lauramine oxide, soyamidopropyl amine oxide, and cocamidopropyl amine oxide; about 0.5 to 4 wt. % PEG-based nonionic surfactant, which includes PEG-80 sorbitan laurate; about 0.5 to 2 wt. % PEG-based nonionic polymer, which includes polymeric polyethyleneglycol distearate; about 0.05 to 0.5 wt. % $C_{10}$-$C_{16}$-fatty acid isopropanolamide; about 0.05 to 0.3 wt. % zwitterionic surfactant, which includes cocamidopropyl PG-dimonium chloride phosphate; about 1 to 5 wt. % polyol humectant, which includes glycerin, sorbitol and/or hexylene glycol; about 0.1 to 1 wt. % cellulose derivative; about 0.1 to 1 wt. % preservative, which includes phenoxyethanol; about 0.5 to 2 wt. % silicone-based skin conditioning agent, which includes PEG-8 dimethicone; and at least about 80 wt. % water.

In some embodiments, the antimicrobial composition may include about 0.3 to 0.8 wt. % of the cationic antimicrobial component; about 0.5 to 1.5 wt. % of the tertiary amine oxide surfactant; about 0.2 to 1 wt. % alkyl glycoside; about 0.05 to about 0.5 wt. % of the C10-C16 fatty acid isopropanolamide; about 0.05 to 0.3 wt. % quaternary ammonium phospholipid zwitterionic surfactant; about 0.5 to 2 wt. % PEG-based nonionic polymer; about 0.5 to 2 wt. % of the water-soluble silicone polymer; about 5 to 12 wt. % humectant; and at least about 80 wt % water. In such embodiments, the combined amount of the tertiary amine oxide surfactants, the isopropanolamide, the zwitterionic surfactant and the alkyl glycoside and/or PEG-based nonionic surfactant may constitute no more than about 2.0 wt. % and, often, no more than about 1.7 wt. % of the composition.

In some embodiments, the compositions may have a pH of about 6 to 7.

In one aspect is provided an antimicrobial composition including: about 0.3 to 1.0 wt. % benzalkonium chloride; about 0.5 to 2 wt. % tertiary amine oxide surfactant, which includes $C_{10}$-$C_{16}$ fatty amine oxide and $C_{10}$-$C_{18}$ fatty acid amidopropyl amine oxide; about 0.5 to 4 wt. % alkyl glycoside and/or PEG-based nonionic surfactant, which includes alkyl glucoside and/or polyethyleneglycol sorbitan fatty acid ester; about 0.5 to 4 wt. % PEG-based nonionic polymer, which includes polyethyleneglycol distearate; about 0.05 to 0.5 wt. % $C_{10}$-$C_{16}$-fatty acid isopropanolamide; about 0.05 to 0.3 wt. % zwitterionic surfactant, which includes cocamidopropyl PG-dimonium chloride phosphate; about 1 to 10 wt. % polyol humectant, which includes glycerin, sorbitol and/or hexylene glycol; about 0.1 to 1 wt. % cellulose derivative; about 0.1 to 1 wt. % preservative, which includes phenoxyethanol; about 0.5 to 2 wt. % silicone-based skin conditioning agent, which includes polyethyleneglycol dimethicone; and at least about 80 wt. % water.

In one aspect, the antimicrobial composition may include: a cationic antimicrobial agent; a surfactant system that includes at least two tertiary amine oxide surfactants, an alkyl glycoside surfactant and a zwitterionic surfactant; humectant(s); emollient(s); foam stabilizing agent(s); and water.

In another aspect, the present technology provides an antimicrobial composition that includes: benzalkonium chloride; at least two tertiary amine oxide surfactants; a zwitterionic surfactant; water soluble cationic and nonionic polymers; an alkyl glucoside surfactant; humectant(s); emollient(s); buffer; solvent(s); and water.

In another aspect, the present technology provides an antimicrobial composition that includes: benzalkonium chloride; at least two tertiary amine oxide surfactants and a cationic surfactant; water soluble cationic and nonionic polymers; an alkyl glucoside surfactant; humectant(s); emollient(s); buffer; solvent(s); and water.

In another aspect is provided an antimicrobial handwashing composition including: benzalkonium chloride present in amounts of greater than about 0.2 wt. %; a surfactant system comprising at least three tertiary amine oxide surfactants, a zwitterionic surfactant, and an isopropanolamide; PEG-80 sorbitan laurate; humectant(s); emollient(s); foam stabilizing agent(s); preservative; thickener; buffer; and water.

In another aspect is provided an antimicrobial handwashing composition including: benzalkonium chloride present in amounts of greater than about 0.2 wt. %; a surfactant system comprising at least three tertiary amine oxide surfactants, a cationic surfactant, and an isopropanolamide; PEG-80 sorbitan laurate; humectant(s); emollient(s); foam stabilizing agent(s); preservative; thickener; buffer; and water.

The present technology provides an antimicrobial composition that includes: benzalkonium chloride present in amounts ranging from about 0.3 to 1 wt. %; a surfactant system including of lauramine oxide, soyamidopropyl amine oxide, cocamidopropyl amine oxide, decyl glucoside, cocamide MIPA and cocamidopropyl PG-dimonium chloride phosphate; skin conditioning agent(s); foam stabilizer(s); and water.

In one aspect, the antimicrobial composition may include: benzalkonium chloride present in amounts ranging from about 0.3 to 1 wt. %; a surfactant system including lauramine oxide, soyamidopropyl amine oxide, cocamidopropyl amine oxide, cocamide MIPA, and cocamidopropyl PG-dimonium chloride phosphate; PEG-80 sorbitan laurate; cellulosic thickener(s); skin conditioning agent(s); foam stabilizer(s); and water.

While certain embodiments have been illustrated and described, it should be understood that changes and modifications can be made therein in accordance with ordinary skill in the art without departing from the technology in its broader aspects.

The embodiments, illustratively described herein may suitably be practiced in the absence of any element or elements, limitation or limitations, not specifically disclosed herein. Thus, for example, the terms "comprising," "including," "containing," shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof.

What is claimed is:

1. An aqueous antimicrobial composition comprising
   a. about 0.3 to 1.0 wt. % benzalkonium antimicrobial;
   b. about 0.5 to 3 wt. % of a tertiary amine oxide surfactant, which comprises lauryl amine oxide, soyamidopropyl amine oxide, and cocamidopropyl amine oxide;
   c. about 0.5 to 2 wt. % of a PEG-based nonionic surfactant;
   d. about 0.1 to 2 wt. % of a $C_{10}$-$C_{12}$ alkyl glycoside nonionic surfactant;
   e. about 0.05 to 0.3 wt. % of a quaternary ammonium phospholipid zwitterionic surfactant comprising cocamidopropyl dimonium chloride phosphate;
   f. about 0.1 to 0.3 wt. % of a $C_{10}$-$C_{16}$ fatty acid isopropanolamide;
   g. about 0.5 to 2 wt. % of a water-soluble silicone polymer;
   h. about 0.1 to 2 wt. % of a cellulose derivative comprising cetyl cellulose and/or hydroxypropyl methylcellulose;
   i. about 0.05 to 0.3 wt. % of a cationic acrylamide-based polymer;
   j. about 0.1 to 2 wt. % of a humectant comprising hexylene glycol, glycerin, and/or sorbitol; and
   at least about 85 wt % water;
   wherein the combined amounts of the tertiary amine oxide surfactant, the isopropanolamide, the zwitterionic surfactant and the nonionic surfactants constitute no more than about 1.7 wt. % of the composition; and the composition has a pH of about 6 to 7.

2. The antimicrobial composition of claim 1, wherein the $C_{10}$-$C_{16}$ fatty acid isopropanolamide comprises cocamide monoisopropanolamide.

3. The antimicrobial composition of claim 1, wherein the water-soluble silicone polymer comprises polyethyleneglycol dimethicone.

4. The antimicrobial composition of claim 1, wherein the alkyl glycoside nonionic surfactant comprises decyl glucoside and/or lauryl glucoside.

5. The antimicrobial composition of claim 1, wherein the composition further comprises one or more of the following: after-feel component, additional antimicrobial, solvent, viscosity modifying agent, preservative, perfume, dye, and buffer.

6. The antimicrobial composition of claim 1, wherein the PEG-based nonionic surfactant comprises polyethyleneglycol fatty acid diester.

7. The aqueous antimicrobial composition of claim 1, wherein the $C_{10}$-$C_{16}$ fatty acid isopropanolamide comprises cocamide monoisopropanolamide; the water-soluble silicone polymer comprises polyethyleneglycol dimethicone; the $C_{10}$-$C_{12}$ alkyl glycoside nonionic surfactant comprises decyl glucoside and/or lauryl glucoside; and the PEG-based nonionic surfactant comprises polyethyleneglycol sorbitan fatty acid ester and/or polyethyleneglycol fatty acid diester.

* * * * *